(12) United States Patent
Lange et al.

(10) Patent No.: US 12,275,901 B2
(45) Date of Patent: Apr. 15, 2025

(54) RECOVERY OF ALIPHATIC HYDROCARBONS

(71) Applicant: SHELL OIL COMPANY, Houston, TX (US)

(72) Inventors: Jean-Paul Andre Marie Joseph Ghislain Lange, Amsterdam (NL); Guus Van Rossum, Amsterdam (NL); Timothé Johannes Olthof, Amsterdam (NL); Kai Jürgen Fischer, Amsterdam (NL); Hendrik Stichter, Amsterdam (NL); Jose Atilio Quevedo Enriquez, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 85 days.

(21) Appl. No.: 18/248,758

(22) PCT Filed: Nov. 12, 2021

(86) PCT No.: PCT/EP2021/081490
§ 371 (c)(1),
(2) Date: Apr. 12, 2023

(87) PCT Pub. No.: WO2022/101394
PCT Pub. Date: May 19, 2022

(65) Prior Publication Data
US 2024/0034942 A1    Feb. 1, 2024

(30) Foreign Application Priority Data
Nov. 3, 2020    (EP) ..................................... 20207478

(51) Int. Cl.
*C10G 55/04*    (2006.01)
*C07C 7/00*    (2006.01)
(Continued)

(52) U.S. Cl.
CPC ................ *C10G 55/04* (2013.01); *C07C 7/10* (2013.01)

(58) Field of Classification Search
None
See application file for complete search history.

(56) References Cited

U.S. PATENT DOCUMENTS 3,963,610 A    6/1976    Hauschulz et al.
9,162,944 B2   10/2015   Bennett et al.
(Continued)

OTHER PUBLICATIONS

International Search Report and Written Opinion Received for PCT Patent Application No. PCT/EP2021/081490, Mailed on Jan. 21, 2022, 12 Pages.

(Continued)

*Primary Examiner* — Tam M Nguyen
(74) *Attorney, Agent, or Firm* — SHELL USA, INC.

(57) ABSTRACT

The invention relates to a process for the recovery of aliphatic hydrocarbons from a liquid stream comprising aliphatic hydrocarbons, heteroatom containing organic compounds and optionally aromatic hydrocarbons, involving a) contacting said liquid stream with a stream having a pH above 7 and comprising a washing solvent, preceded and/or followed by contacting with a stream having a pH below 7 and comprising a washing solvent; b) liquid-liquid extraction of the washed stream with an extraction solvent. Further, the invention relates to a process for the recovery of aliphatic hydrocarbons from plastics comprising the above-mentioned process; and to a process for steam cracking a hydrocarbon feed comprising aliphatic hydrocarbons as recovered in one of the above-mentioned processes.

10 Claims, 2 Drawing Sheets

(51) Int. Cl.
  *C07C 7/08* (2006.01)
  *C07C 7/10* (2006.01)
  *C10G 7/10* (2006.01)

(56) References Cited

U.S. PATENT DOCUMENTS

| | | | |
|---|---|---|---|
| 10,130,896 | B2 | 11/2018 | Saukonoja et al. |
| 10,738,264 | B2 | 8/2020 | Bergström et al. |
| 10,927,315 | B2 | 2/2021 | Ramamurthy et al. |
| 11,427,782 | B2 | 8/2022 | Toukoniitty et al. |
| 2009/0148920 | A1* | 6/2009 | Schreck ............... C11C 3/003 560/191 |
| 2018/0187087 | A1 | 7/2018 | Atkins et al. |
| 2018/0355256 | A1 | 12/2018 | Dooley |
| 2021/0292657 | A1 | 9/2021 | Toukoniitty et al. |
| 2022/0177786 | A1 | 6/2022 | Lange et al. |
| 2022/0195315 | A1 | 6/2022 | Zhang et al. |
| 2023/0193419 | A1* | 6/2023 | Monzyk ............... C22B 26/12 423/179.5 |
| 2023/0365877 | A1* | 11/2023 | Lange ............... C10G 1/10 |
| 2023/0392088 | A1* | 12/2023 | Lange ............... C10G 53/08 |

OTHER PUBLICATIONS

Xiao et al., "Chemical Dechlorination of Hexachlorobenzene With Polyethylene Glycol and Hydroxide: Dominant Effect of Temperature and Ionic Potential", Scientific Reports, Sep. 9, 2014, vol. 4, pp. 1-6.

Khan, "Bleaching of Vegetable Oil using Organic Acid Activated Fuller's Earth (Bentonite Clay)", Global Journal of Researches in Engineering : C Chemical Engineering, 2015, vol. 15, Issue No. 2, 7 Pages.

Venkatram et al., "Critical Assessment of the Hildebrand and Hansen Solubility Parameters for Polymers", Journal of Chemical Information and Modeling, Sep. 23, 2019, vol. 59, pp. 4188-4194.

Scheirs et al., "Overview of Commercial Pyrolysis Processes for Waste Plastics", Feedstock Recycling and Pyrolysis of Waste Plastics: Converting Waste Plastics into Diesel and Other Fuels, 2006, pp. 383-431, XP002717509.

Inoue et al., "Purification of Oils and Fats by Ion-Exchange Resins. III. Ultraviolet Absorption Spectra of Deacidified Oils and Adsorbed Components", Journal of Japan Oil Chemists' Society, 1961, vol. 10, Issue No. 11, pp. 16-21.

* cited by examiner

RECOVERY OF ALIPHATIC HYDROCARBONS

CROSS REFERENCE TO RELATED APPLICATIONS

This is a National stage application of International Application No. PCT/EP2021/081490, filed 12 Nov. 2021, which claims priority of European Patent Application No. 20207478.7, filed 13 Nov. 2020 which are incorporated herein by reference in their entirety.

FIELD OF THE INVENTION

The present invention relates to a process for the recovery of aliphatic hydrocarbons from a liquid hydrocarbon feedstock stream comprising aliphatic hydrocarbons, heteroatom containing organic compounds and optionally aromatic hydrocarbons; to a process for the recovery of aliphatic hydrocarbons from plastics comprising the above-mentioned process; and to a process for steam cracking a hydrocarbon feed comprising aliphatic hydrocarbons as recovered in one of the above-mentioned processes.

BACKGROUND OF THE INVENTION

Waste plastics can be converted via cracking of the plastics, for example by pyrolysis, to high-value chemicals, including olefins and aromatic hydrocarbons. Pyrolysis of plastics can yield product streams containing hydrocarbons in a wide boiling range. Hydrocarbons from such pyrolysis product streams can be further cracked in a steam cracker to produce high-value chemicals, including ethylene and propylene which are monomers that can be used in making new plastics.

WO2020212315 discloses a process for the recovery of aliphatic hydrocarbons from a liquid hydrocarbon feedstock stream comprising aliphatic hydrocarbons and additionally comprising aromatic hydrocarbons and/or polar components, said process comprising feeding the feedstock stream and an organic solvent stream to a column; contacting the feedstock stream with the organic solvent stream; and recovering aliphatic hydrocarbons by liquid-liquid extraction of aromatic hydrocarbons and/or polar components with the organic solvent.

According to above-mentioned WO2020212315, said liquid hydrocarbon feedstock stream may comprise a liquid product produced by the pyrolysis of plastic waste. Further, according to WO2020212315, said organic solvent may be selected from the group consisting of diols and triols, including monoethylene glycol, monopropylene glycol and any isomer of butanediol; glycol ethers, including oligoethylene glycols, including diethylene glycol and tetraethylene glycol, and ethers thereof, including diethylene glycol dimethylether; amides, including N-alkylpyrrolidone, including N-methylpyrrolidone, and dialkyl formamide, including dimethyl formamide; dialkylsulfoxide, including dimethylsulfoxide; sulfolane; N-formyl morpholine (NFM); and furan ring containing components, including furfural, 2-methyl-furan and furfuryl alcohol.

Further, US20180355256 discloses a method for deriving fuel from plastics, the method comprising subjecting a quantity of plastics to a pyrolytic process, thereby to convert at least part of the plastics to a crude fuel; and extracting the fuel in a directly usable form by way of: 1) a first extraction step comprising counterflow liquid-liquid extraction using one or more extraction solvents to extract one or more impurities from the crude fuel; and 2) a second extraction step comprising counterflow extraction of resultant contaminated extraction solvent(s) from the first extraction step. In the process as shown in FIG. 2 of US20180355256, a crude fuel (i.e. a crude diesel) that is made by pyrolysis of plastics, is first subjected to extraction with N-methyl-2-pyrrolidone (NMP) to extract one or more impurities, including sulfur compounds and aromatics, from the crude fuel. The contaminated NMP from the first extraction step is then subjected to a second extraction step using water, to increase the polarity of the contaminated extraction solvent, thereby separating off said impurities. In a final step, the water-contaminated NMP from the second extraction step is distilled using a standard distillation column, which gives rise to recycle water and recycle NMP.

Even though in the process of above-mentioned US20180355256, a certain amount of heteroatom containing organic contaminants may be removed from the crude fuel (feedstock) in the first extraction step, the resulting purified fuel may still comprise a relatively high amount of these contaminants, which is of particular concern when such cleaned oil would be fed to a steam cracker, instead of being used as a fuel, because of the negative impact of these contaminants on the yield, selectivity and reliability of steam crackers.

In addition, such crude feedstock may contain other contaminants, for example silicon containing compounds, such as silica and siloxane compounds. For example, said silica is known for its use as a filler material, for example glass fiber ($SiO_2$), improving the mechanical properties of plastics. Further, said siloxane compounds may originate from polysiloxane polymers which contain —$R_2Si$—O—$SiR_2$— chains. It may be that such silicon containing compounds are not removed by an extraction solvent (such as NMP) and hence end up in the raffinate stream. Further, other contaminants in such crude feedstock may be metals. For example, calcite ($CaCO_3$) and wollastonite ($CaSiO_2$) are also known for their use as a filler material in plastics. A part of these metals may not end up in the extract stream but may form a complex with an extraction solvent and end up in the raffinate stream instead. Such silicon containing compounds and metals from a raffinate stream also have a negative impact when present in the feed to a steam cracker because of the fouling of tube furnaces they may cause in a steam cracker furnace.

Generally, there are certain specifications (maximum concentrations) for a number of heteroatom containing organic contaminants, especially chloride, nitrogen and/or oxygen containing contaminants, and for other contaminants such as above-mentioned silicon containing compounds and metals, that a hydrocarbon feed should meet before it may be fed into a steam cracker.

There may be crude feeds to an extraction process like the one as disclosed in above-mentioned US20180355256, which contain such high amount of heteroatom containing organic contaminants and any other contaminants, for example pyrolysis oil made from waste plastics, so high that only applying such extraction process does not result in a purified feed (e.g. to a steam cracker) which is of sufficient quality that would meet above-mentioned specifications.

In addition, in said extraction process, there may be a "build-up" of said contaminants in the recycle water (extraction solvent in second extraction step) and recycle NMP (extraction solvent in first extraction step), which eventually leads to a further reduction of the quality of the final purified product.

The above-mentioned build-up of contaminants may be caused by extracting also part of the contaminants in the second extraction step, in addition to the NMP to be extracted, by the water extraction solvent in the process of above-mentioned US20180355256. As a consequence, the feed to the distillation column (in FIG. 2 of US20180355256) may still comprise a certain amount of heteroatom containing organic contaminants, especially oxygen containing organic contaminants, in particular the more polar components including e.g. phenol. Said distillation may result in that part of said contaminants is separated off together with the recycle water because water and such contaminants may form an azeotrope, thereby reducing the quality of the water recycle stream. In case that recycle water is recycled to the column used in the second extraction step, the concentration of these contaminants in the recycle water will increase (build-up), in addition to a build-up of these contaminants in the recycle NMP to be used in the first extraction step. This can result in a reduced efficiency of the first and second extraction steps. Such build-up of these contaminants (in said recycle NMP) may result in that the cleaned oil still comprises a relatively high amount of these contaminants, which is of particular concern when such cleaned oil would be fed to a steam cracker.

Furthermore, in practice, the feedstock may comprise other contaminants such as salts, especially a liquid hydrocarbon feedstock stream obtained from pyrolysis of plastics. For example, such feedstock may contain calcite ($CaCO_3$) and wollastonite ($CaSiO_3$), as discussed above. Such salts may end up in an extract stream, for example in a case wherein the extraction solvent is NMP as used in column A of the process of FIG. 2 of U520180355256. Subsequently, such salts would end up in the water-NMP bottom stream from column B used in said process, and then enter distillation column C where they will concentrate in the NMP bottom stream. The salts will then be recycled together with the NMP and their concentration will build up over time. Furthermore, since NMP and other organic solvents have a limited solvency for salts, they will start precipitating in the distillation column resulting in fouling of the column.

There is an ongoing need to develop improved processes for the recovery of aliphatic hydrocarbons from liquid streams comprising aliphatic hydrocarbons, heteroatom containing organic compounds and optionally aromatic hydrocarbons which may originate from cracking waste plastics, in specific mixed waste plastics, especially before feeding such recovered aliphatic hydrocarbons to a steam cracker. It is an object of the present invention to provide such process for the recovery of aliphatic hydrocarbons from such liquid streams, which process is technically advantageous, efficient and affordable, in particular a process which does not have one or more of the above-mentioned disadvantages, as discussed above in connection with US20180355256. Such technically advantageous process would preferably result in a relatively low energy demand and/or relatively low capital expenditure.

SUMMARY OF THE INVENTION

Surprisingly it was found by the present inventors that such process can be provided by a) contacting a liquid stream which comprises aliphatic hydrocarbons, heteroatom containing organic compounds and optionally aromatic hydrocarbons, with a stream having a pH above 7 and comprising a washing solvent a) which contains one or more heteroatoms, preceded and/or followed by contacting with a stream having a pH below 7 and comprising washing solvent a), thereby removing heteroatom containing organic compounds; and b) liquid-liquid extraction of a stream resulting from washing step a) which comprises aliphatic hydrocarbons, heteroatom containing organic compounds and optionally aromatic hydrocarbons, with an extraction solvent b) which contains one or more heteroatoms.

Accordingly, the present invention relates to a process for the recovery of aliphatic hydrocarbons from a liquid hydrocarbon feedstock stream comprising aliphatic hydrocarbons, heteroatom containing organic compounds and optionally aromatic hydrocarbons, said process comprising the steps of:

a) mixing at least part of the liquid hydrocarbon feedstock stream with a stream having a pH above 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, said step a) further comprising:

a1) before mixing with the stream having a pH above 7: mixing at least part of the liquid hydrocarbon feedstock stream with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and mixing at least part of said second stream with the stream having a pH above 7, and/or a2) after mixing with the stream having a pH above 7: mixing at least part of the second stream, resulting from the mixing with the stream having a pH above 7 and the separation into first and second streams, with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and feeding at least part of said second stream to step b); and b) contacting at least part of the second stream resulting from step a) with an extraction solvent b) which contains one or more heteroatoms and subjecting that stream to liquid-liquid extraction with extraction solvent b), resulting in a first stream comprising aliphatic hydrocarbons and optionally heteroatom containing organic compounds and a second stream comprising extraction solvent b), heteroatom containing organic compounds and optionally aromatic hydrocarbons.

Advantageously, in the present invention, heteroatom containing organic compounds and optionally said other contaminants that may end up in the final purified hydrocarbon product by only applying an extraction step, are removed by the washing step in the process of the present invention, which washing step includes multiple washing steps of which at least one is performed at a pH above 7 ("alkaline") and at least one is performed at a pH below 7 ("acid"). This in turn, advantageously, may result in a final hydrocarbon product which is of sufficiently high quality that it meets certain specifications (maximum concentrations) for a number of heteroatom containing organic contaminants, especially chloride, nitrogen and/or oxygen containing contaminants, and for any other contaminants, that a hydrocarbon feed should meet before it may be fed into a steam cracker. Within the present specification, by said "other contaminants", other than heteroatom containing organic contaminants (heteroatom containing organic compounds) in or originating from the liquid hydrocarbon feedstock stream, reference is made to contaminants that may comprise salts and/or silicon containing compounds and/or metals in or originating from the liquid hydrocarbon feedstock stream.

Further, advantageously, part of the heteroatom containing organic compounds, especially oxygen containing organic contaminants, in particular the more polar components including e.g. phenol, are removed in washing step a) preceding extraction step b), in which step a) at least part of the liquid hydrocarbon feedstock stream is contacted with washing solvent a), first at a high pH (>7) then at a low pH (<7) or vice versa, that is to say first at a low pH (<7) then at a high pH (>7), thereby avoiding or reducing a build-up of such contaminants in the downstream part of the present process. Between said acid and alkaline washing steps, there may be an intermediate rinsing step wherein a neutral washing solvent stream (pH of about 7) is used. Furthermore, advantageously, in said washing step a) any other contaminants from the feedstock stream are also removed, thereby preventing a build-up of some of these other contaminants, including salts, to higher concentrations in the downstream section, and thereby at the same time preventing fouling of a downstream distillation column by precipitation of such salts.

Further, the extracted heteroatom containing organic compounds and optionally said other contaminants in the second (extract) stream resulting from step b), comprising extraction solvent b), heteroatom containing organic compounds and optionally aromatic hydrocarbons, may build up in any recycle extraction solvent b) stream to said step b), as discussed above. Said heteroatom containing organic compounds that cause such build up, may comprise the components with the highest polarity of all the heteroatom containing organic compounds as extracted in step b) of the present process. In such case, advantageously, through washing step a), part of these heteroatom containing organic compounds and other optional contaminants are already removed from the feedstock stream before being subjected to extraction step b), thereby preventing said build-up in any extraction solvent b) recycle stream. A relatively pure extraction solvent b) stream can then advantageously be recycled to step b) and used to extract further heteroatom containing organic compounds and optional aromatic hydrocarbons from fresh feed. Thus, in the present invention, the above-mentioned contaminants, including heteroatom containing organic compounds and any other contaminants, including any salts, that build up or could build up as discussed above, may advantageously already be removed in washing step a) which precedes extraction step b), thereby preventing a build-up of such contaminants in any recycle stream in the present process and eventually resulting in a relatively pure final hydrocarbon product.

Because of the above-described pre-washing step a), in the present invention there is no need or a substantially reduced need to apply other, cumbersome methods for mitigating a build-up of these contaminants. For example, there is no need or a substantially reduced need to bleed part of any recycle stream (e.g. any recycle extraction solvent b) stream) before recycling, wherein either (i) such bleed stream is discarded resulting in a loss of extraction solvent or (ii) the extraction solvent may be recovered from such bleed stream, for example by distillation thereof, which is however cumbersome.

In addition, in the above-described washing step a) in the process of the present invention, other contaminants which should preferably not end up in the raffinate stream resulting from extraction step b), may advantageously also be removed simultaneously with the above-mentioned heteroatom containing organic contaminants and optional salts. For example, the above-mentioned metals and silicon containing compounds, such as silica and siloxane compounds, may advantageously also be removed in step a) of the present process, thereby preventing any negative impact that such contaminants may have in a subsequent process, such as a steam cracking process. For, in said step a), the acid stream (pH below 7) comprising washing solvent a) may advantageously remove heteroatom containing organic compounds and/or metals, whereas the alkaline stream (pH above 7) comprising washing solvent a) may advantageously remove heteroatom containing organic compounds and/or silicon containing compounds.

Further, the present invention relates to a process for the recovery of aliphatic hydrocarbons from plastics, wherein at least part of the plastics comprises heteroatom containing organic compounds, said process comprising the steps of:
(I) cracking the plastics and recovering a hydrocarbon product comprising aliphatic hydrocarbons, heteroatom containing organic compounds and optionally aromatic hydrocarbons; and
(II) subjecting a liquid hydrocarbon feedstock stream, which comprises at least part of the hydrocarbon product obtained in step (I), to the above-mentioned process for the recovery of aliphatic hydrocarbons from a liquid hydrocarbon feedstock stream.

Still further, the present invention relates to a process for steam cracking a hydrocarbon feed, wherein the hydrocarbon feed comprises aliphatic hydrocarbons as recovered in one of the above-mentioned processes for the recovery of aliphatic hydrocarbons.

DETAILED DESCRIPTION OF THE INVENTION

Figure 1:
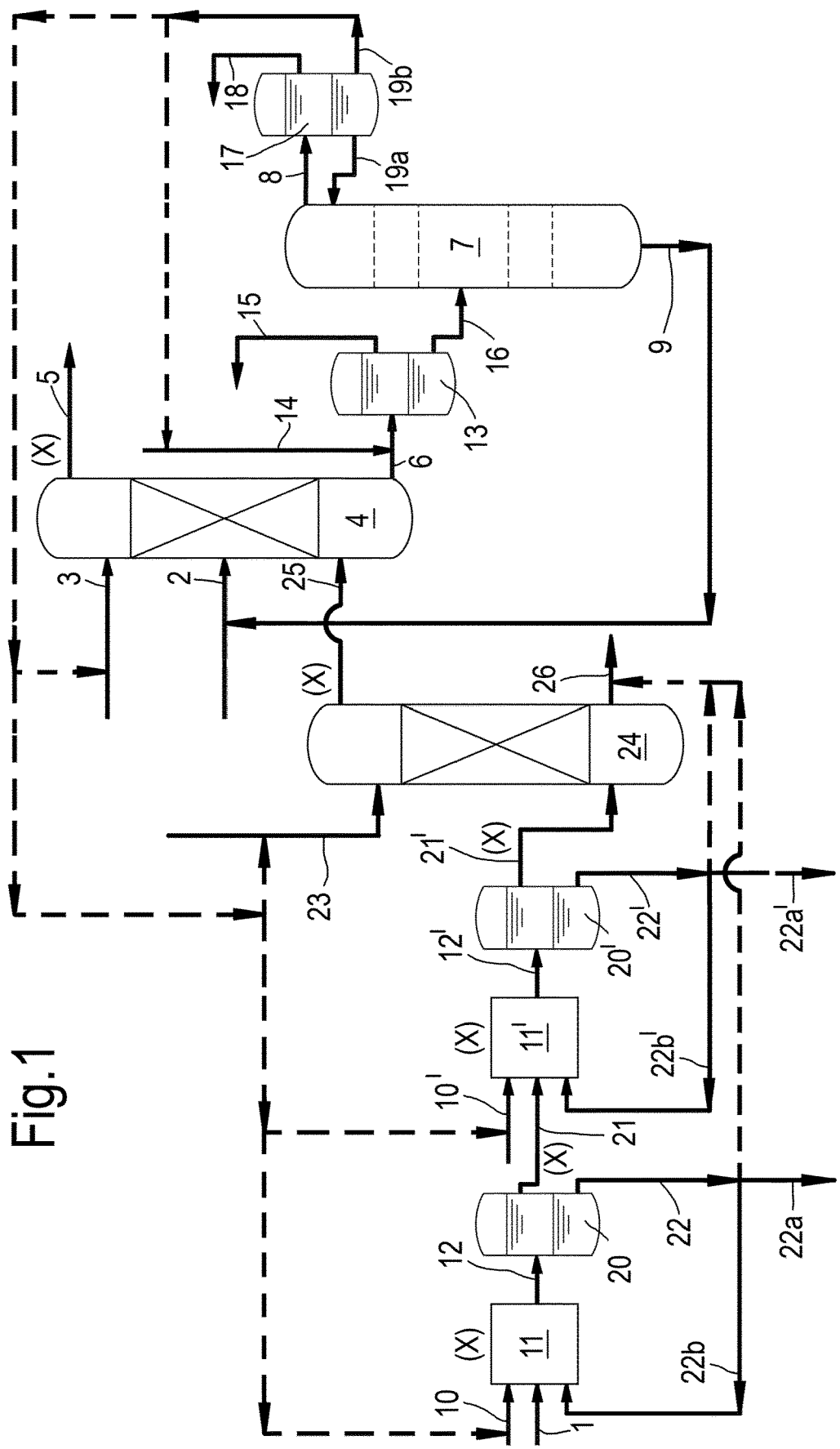
FIG. 1 shows one embodiment of the process for the recovery of aliphatic hydrocarbons in accordance with the present invention.

Each of the processes of the present invention comprises multiple steps. In addition, said process may comprise one or more intermediate steps between consecutive steps. Further, said process may comprise one or more additional steps preceding the first step and/or following the last step. For example, in a case where said process comprises steps a), b) and c), said process may comprise one or more intermediate steps between steps a) and b) and between steps b) and c). Further, said process may comprise one or more additional steps preceding step a) and/or following step c).

Within the present specification, a phrase like "step y) comprises subjecting at least part of the stream resulting from step x) to" means "step y) comprises subjecting part or all of the stream resulting from step x) to" or, similarly, "step y) comprises partially or completely subjecting the stream resulting from step x) to". For example, the stream resulting from step x) may be split into one or more parts wherein at least one of these parts may be subjected to step y). Further, for example, the stream resulting from step x) may be subjected to an intermediate step between steps x) and y) resulting in a further stream at least part of which may be subjected to step y).

While the process(es) of the present invention and the stream(s) and composition(s) used in said process(es) are described in terms of "comprising", "containing" or "including" one or more various described steps and components, respectively, they can also "consist essentially of" or "consist of" said one or more various described steps and components, respectively.".

In the context of the present invention, in a case where a stream comprises two or more components, these components are to be selected in an overall amount not to exceed 100%.

Further, where upper and lower limits are quoted for a property then a range of values defined by a combination of any of the upper limits with any of the lower limits is also implied.

Within the present specification, by "substantially no" in relation to the amount of a specific component in a stream, it is meant an amount which is at most 1,000, preferably at most 500, more preferably at most 100, more preferably at most 50, more preferably at most 30, more preferably at most 20, and most preferably at most 10 ppmw (parts per million by weight) of the component in question, based on the amount (i.e. weight) of said stream.

Within the present specification, by "top stream" or "bottom stream" from a column reference is made to a stream which exits the column at a position, which is between 0% and 30%, more suitably between 0% and 20%, even more suitably between 0% and 10%, based on the total column length, from the top of the column or the bottom of the column, respectively.

Unless indicated otherwise, where in the present specification reference is made to a boiling point this means the boiling point at 760 mm Hg pressure (101.3 kPa).

Within the present specification, the term "heteroatom containing compounds" refers to heteroatom containing organic compounds and/or heteroatom containing inorganic compounds including salts.

Liquid Hydrocarbon Feedstock Stream

In the present invention, the liquid hydrocarbon feedstock stream comprises aliphatic hydrocarbons, heteroatom containing organic compounds and optionally aromatic hydrocarbons.

Preferably, the liquid hydrocarbon feedstock stream comprises both aliphatic hydrocarbons having a boiling point of from 30 to 300° C. and aliphatic hydrocarbons having a boiling point of from greater than 300 to 600° C. in a weight ratio of from 99:1 to 1:99. The amount of aliphatic hydrocarbons having a boiling point of from 30 to 300° C., based on the total amount of aliphatic hydrocarbons having a boiling point of from 30 to 600° C., may be at most 99 wt. % or at most 80 wt. % or at most 60 wt. % or at most 40 wt. % or at most 30 wt. % or at most 20 wt. % or at most 10 wt. %. Further, the amount of aliphatic hydrocarbons having a boiling point of from 30 to 300° C., based on the total amount of aliphatic hydrocarbons having a boiling point of from 30 to 600° C., may be at least 1 wt. % or at least 5 wt. % or at least 10 wt. % or at least 20 wt. % or at least 30 wt. %.

Thus, advantageously, the liquid hydrocarbon feedstock stream may comprise varying amounts of aliphatic hydrocarbons within a wide boiling point range of from 30 to 600° C. Accordingly, as with the boiling point, the carbon number of the aliphatic hydrocarbons in the liquid hydrocarbon feedstock stream may also vary within a wide range, for example of from 5 to 50 carbon atoms. The carbon number of the aliphatic hydrocarbons in the liquid hydrocarbon feedstock stream may be at least 4 or at least 5 or at least 6 and may be at most 50 or at most 40 or at most 30 or at most 20.

The amount of aliphatic hydrocarbons in the liquid hydrocarbon feedstock stream, based on the total weight of the liquid hydrocarbon feedstock stream, may be at least 30 wt. % or at least 50 wt. % or at least 80 wt. % or at least 90 wt. % or at least 95 wt. % or at least 99 wt. % and may be smaller than 100 wt. % or at most 99 wt. % or at most 90 wt. % or at most 80 wt. % or at most 70 wt. %. The aliphatic hydrocarbons may be cyclic, linear and branched.

The aliphatic hydrocarbons in the liquid hydrocarbon feedstock stream may comprise non-olefinic (paraffinic) and olefinic aliphatic compounds. The amount of paraffinic aliphatic compounds in the liquid hydrocarbon feedstock stream, based on the total weight of the liquid hydrocarbon feedstock stream, may be at least 20 wt. % or at least 40 wt. % or at least 60 wt. % or at least 80 wt. % and may be smaller than 100 wt. % or at most 99 wt. % or at most 80 wt. % or at most 60 wt. %. Further, the amount of olefinic aliphatic compounds in the liquid hydrocarbon feedstock stream, based on the total weight of the liquid hydrocarbon feedstock stream, may be smaller than 100 wt. % or at least 20 wt. % or at least 40 wt. % or at least 60 wt. % or at least 80 wt. % and may be at most 99 wt. % or at most 80 wt. % or at most 60 wt. %.

Further, the olefinic compounds may comprise aliphatic compounds having one carbon-carbon double bond (mono-olefins) and/or aliphatic compounds having two or more carbon-carbon double bonds which latter compounds may be conjugated or non-conjugated. That is to say, the two or more carbon-carbon double bonds may be conjugated or not conjugated. The aliphatic compounds having two or more carbon-carbon double bonds may include compounds having double bonds at alpha and omega positions. The amount of mono-olefins in the liquid hydrocarbon feedstock stream, based on the total weight of the liquid hydrocarbon feedstock stream, may be at least 20 wt. % or at least 40 wt. % or at least 60 wt. % or at least 80 wt. % and may be smaller than 100 wt. % or at most 99 wt. % or at most 80 wt. % or at most 60 wt. %. Further, the amount of conjugated aliphatic compounds having two or more carbon-carbon double bonds in the liquid hydrocarbon feedstock stream, based on the total weight of the liquid hydrocarbon feedstock stream, may be greater than 0 wt. % or at least 10 wt. % or at least 20 wt. % or at least 40 wt. % or at least 60 wt. % and may be at most 80 wt. % or at most 60 wt. % or at most 40 wt. %.

Within the present specification, an aliphatic hydrocarbon which contains one or more heteroatoms is a "heteroatom containing organic compound" as further described below. Unless indicated otherwise, either explicitly or by context, within the present specification, the term "aliphatic hydrocarbons" does not include heteroatom containing aliphatic hydrocarbons. Further, unless indicated otherwise, either explicitly or by context, within the present specification, the term "aliphatic hydrocarbons" does not include conjugated aliphatic compounds having two or more carbon-carbon double bonds.

In addition to the above-described aliphatic hydrocarbons, the liquid hydrocarbon feedstock stream comprises heteroatom containing organic compounds and optionally aromatic hydrocarbons.

The amount of aromatic hydrocarbons in the liquid hydrocarbon feedstock stream, based on the total weight of the liquid hydrocarbon feedstock stream, may be 0 wt. % or greater than 0 wt. % or at least 5 wt. % or at least 10 wt. % or at least 15 wt. % or at least 20 wt. % or at least 25 wt. % or at least 30 wt. % and may be at most 50 wt. % or at most 40 wt. % or at most 30 wt. % or at most 20 wt. %. The aromatic hydrocarbons may comprise monocyclic and/or polycyclic aromatic hydrocarbons. An example of a monocyclic aromatic hydrocarbon is styrene. The polycyclic aromatic hydrocarbons may comprise non-fused and/or fused polycyclic aromatic hydrocarbons. An example of a non-fused polycyclic aromatic hydrocarbon is oligostyrene. Styrene and oligostyrene may originate from polystyrene. Examples of fused polycyclic aromatic hydrocarbons are naphthalene and anthracene, as well as alkyl naphthalene and alkyl anthracene. The aromatic ring or rings in the aromatic hydrocarbons may be substituted by one or more hydrocarbyl groups, including alkyl groups (saturated) and alkylene groups (unsaturated).

Within the present specification, an aromatic hydrocarbon which contains one or more heteroatoms is a "heteroatom containing organic compound" as further described below. Unless indicated otherwise, either explicitly or by context, within the present specification, the term "aromatic hydrocarbons" does not include heteroatom containing aromatic hydrocarbons.

Further, the amount of heteroatom containing organic compounds in the liquid hydrocarbon feedstock stream, based on the total weight of the liquid hydrocarbon feedstock stream, is greater than 0 wt. % and may be at least 0.5 wt. % or at least 1 wt. % or at least 3 wt. % or at least 5 wt. % or at least 10 wt. % or at least 15 wt. % or at least 20 wt. % and may be at most 30 wt. % or at most 20 wt. % or at most 10 wt. % or at most 5 wt. %.

The heteroatom containing organic compounds in the liquid hydrocarbon feedstock stream contain one or more heteroatoms, which may be oxygen, nitrogen, sulfur and/or a halogen, such as chlorine, suitably oxygen, nitrogen and/or a halogen. The heteroatom containing organic compounds may comprise one or more of the following moieties: amine, imine, nitrile, alcohol, ether, ketone, aldehyde, ester, acid, amide, carbamate (occasionally named urethane) and urea.

Further, the above-mentioned heteroatom containing organic compounds may be aliphatic or aromatic. An example of an aliphatic, heteroatom containing organic compound is oligomeric polyvinyl chloride (PVC). Oligomeric PVC may originate from polyvinyl chloride. Aromatic, heteroatom containing organic compounds may comprise monocyclic and/or polycyclic aromatic, heteroatom containing organic compounds. Examples of monocyclic aromatic, heteroatom containing organic compounds are terephthalic acid and benzoic acid. An example of a polycyclic aromatic, heteroatom containing organic compound is oligomeric polyethylene terephthalate (PET). Terephthalic acid, benzoic acid and oligomeric PET may originate from polyethylene terephthalate. Examples of nitrogen containing organic compounds are compounds originating from polyurethane and polyamides including nylon.

Unless indicated otherwise, either explicitly or by context, within the present specification, the term "heteroatom containing organic compounds" means heteroatom containing organic compounds in or originating from the liquid hydrocarbon feedstock stream. Further, unless indicated otherwise, either explicitly or by context, within the present specification, the term "heteroatom containing organic compounds" does not include the extraction solvent and/or washing solvent as defined in the present specification.

Additionally, the liquid hydrocarbon feedstock stream may comprise salts. Said salts may comprise organic and/or inorganic salts. The salts may comprise ammonium, an alkali metal, an alkaline earth metal or a transition metal as the cation and a carboxylate, sulphate, phosphate or a halide as the anion.

Further, additionally, the liquid hydrocarbon feedstock stream may comprise silicon containing compounds, such as silica and siloxane compounds.

Still further, additionally, the liquid hydrocarbon feedstock stream may comprise metals.

Preferably, at least part of the components in the liquid hydrocarbon feedstock stream, which comprises aliphatic hydrocarbons, heteroatom containing organic compounds and optionally aromatic hydrocarbons, are synthetic compounds, and not natural compounds as present in for example fossil oil. For example, such synthetic compounds include compounds originating from the pyrolysis of plastics synthesized from biomass, for example polyethylene synthesized from bio-ethanol through dehydration of the ethanol and subsequent polymerization of the ethylene thus formed.

Further, since in the present process heteroatom containing organic compounds and any other contaminants are easily removed, the feed to the present process can advantageously tolerate a relatively high amount of such heteroatom containing organic compounds and other contaminants. Thus, waste plastic that may be pyrolyzed to produce a feed to the present process may comprise heteroatom-containing plastics, such as polyvinyl chloride (PVC), polyethylene terephthalate (PET) and polyurethane (PU). In specific, mixed waste plastic may be pyrolyzed that in addition to heteroatom-free plastics, such as polyethylene (PE) and polypropylene (PP), contains a relatively high amount of such heteroatom-containing plastics.

Step a)—Pre-Wash of Liquid Hydrocarbon Feedstock Stream

In step a) of the present process, before extraction step b), heteroatom containing organic compounds and optionally other contaminants are removed from the liquid hydrocarbon feedstock stream by contacting at least part of that stream with a washing solvent a). Thus, step a) precedes extraction step b) of the present process.

Step a) comprises mixing at least part of the liquid hydrocarbon feedstock stream with a stream having a pH above 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons. At least part of the second stream resulting from step a) is fed to step b), that is to say contacted with an extraction solvent b) in step b).

Further, in step a) of the present process, in addition to and separately from a washing step using a stream comprising washing solvent a) and having a pH above 7 ("alkaline"), a washing step using a stream comprising washing solvent a) and having a pH below 7 ("acid") is also performed. Said alkaline and acid washing steps in step a) may be performed in any order. However, it is preferred that in step a) first an acid washing step is performed, followed by an alkaline washing step.

Accordingly, in addition to and separately from the alkaline washing step, step a) of the present process further comprises:
- a1) before mixing with the stream having a pH above 7: mixing at least part of the liquid hydrocarbon feedstock stream with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and mixing at least part of said second stream with the stream having a pH above 7, and/or
- a2) after mixing with the stream having a pH above 7: mixing at least part of the second stream, resulting from the mixing with the stream having a pH above 7 and the separation into first and second streams, with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and feeding at least part of said second stream to step b).

Further, in the present process, each of the washing steps in step a) may be performed multiple times in series, that is to say at least two times, preferably two or three times, more preferably two times. The latter implies that the second stream comprising aliphatic hydrocarbons, heteroatom containing organic compounds, optionally other contaminants and optionally aromatic hydrocarbons resulting from a first step a) (or preceding step a)) is sent to a second step a) (or subsequent step a)) wherein further heteroatom containing organic compounds and optionally other contaminants are removed from that second stream by contacting at least part of that stream with washing solvent a), which second step a) also comprises mixing at least part of that stream with washing solvent a) and separating the resulting mixture into a first stream comprising washing solvent a), heteroatom containing compounds and optionally other contaminants and a second stream comprising aliphatic hydrocarbons, heteroatom containing organic compounds and optionally aromatic hydrocarbons. At least part of the second stream resulting from said second step a) is fed to step b), that is to say contacted with an extraction solvent b) in step b), or to a further step a). Further, at least part of the first stream resulting from said second step a) (or from any subsequent step a)) may be fed to said first step a) (or to any preceding step a)), such as to provide washing solvent a) to such first or preceding step a).

Depending on the partition coefficient, heteroatom containing organic compounds and any aromatic hydrocarbons also end up in the second stream resulting from step a) to a certain extent, wherein the second stream is more hydrophobic than the first stream. Thus, said second stream additionally comprises heteroatom containing organic compounds and optionally aromatic hydrocarbons, in addition to aliphatic hydrocarbons. Said first and second streams may additionally comprise conjugated aliphatic compounds having two or more carbon-carbon double bonds.

In step a), washing solvent a) is added, separately from the liquid hydrocarbon feedstock stream and in addition to any washing solvent a), for example water, that may be present in the latter stream, and mixed with the latter stream. In step a), it is preferred that a stream comprising washing solvent a) to be added comprises no or substantially no heteroatom containing organic compounds and no or substantially no other contaminants to be removed from the liquid hydrocarbon feedstock stream, thereby enhancing the efficiency of removing such contaminants from the liquid hydrocarbon feedstock stream.

In step a) of the present process, at least part of the liquid hydrocarbon feedstock stream is contacted with a washing solvent a). In addition, in step a), said stream may also be contacted, preferably simultaneously, with a sorption agent as further described below with reference to sorption step (i).

The washing solvent a) in step a) contains one or more heteroatoms, which may be oxygen, nitrogen and/or sulfur. It is preferred that said washing solvent a) has no or a relatively low miscibility in heptane. Preferably, washing solvent a) has such miscibility in heptane that at most 10 wt. % or at most 3 wt. % or at most 1 wt. % or at most 0.5 wt. % or at most 0.1 wt. % of washing solvent a), based on weight of heptane, is miscible in heptane. Further, it is preferred that the miscibility of washing solvent a) in heptane is lower than the miscibility of extraction solvent b) in heptane. The miscibility of a certain compound in another compound, such as heptane, may be determined by any general method known to a skilled person in the art, including ASTM method D1476. Where in the present specification reference is made to the miscibility of a compound in another compound, this means miscibility at 25° C.

Washing solvent a) in step a) may have a Hansen solubility parameter distance $R_{a,heptane}$ with respect to heptane as determined at 25° C. of at least 10 MPa$^{1/2}$, preferably at least 20 MPa$^{1/2}$, more preferably at least 30 MPa$^{1/2}$, more preferably at least 40 MPa$^{1/2}$. Further, said $R_{a,heptane}$ for washing solvent a) may be at most 55 MPa$^{1/2}$, more preferably at most 50 MPa$^{1/2}$, more preferably at most 45 MPa$^{1/2}$. For example, said $R_{a,heptane}$ for water is 45 MPa$^{1/2}$. Hansen solubility parameters are further described hereinbelow in relation to extraction solvent b) used in step b).

Further, washing solvent a) in step a) may have a solubility of sodium chloride, in g of NaCl per 100 g of solvent as determined at 25° C., of at least 0.1 g/100 g, preferably at least 0.3 g/100 g, more preferably at least 0.5 g/100 g, more preferably at least 0.7 g/100 g, more preferably at least 1 g/100 g, more preferably at least 2 g/100 g, more preferably at least 3 g/100 g, more preferably at least 4 g/100 g and most preferably at least 5 g/100 g, and may be at most 50 g/100 g or at most 40 g/100 g or at most 36 g/100 g. For example, said solubility of sodium chloride for water is 36 g/100 g.

Still further, washing solvent a) in step a) may comprise one or more solvents selected from the group consisting of water, ammonia and organic solvents having a Hansen solubility parameter distance $R_{a,DEAA}$ with respect to diethylammonium acetate (DEAA) as determined at 25° C. of at most 15 MPa$^{1/2}$, preferably at most 13 MPa$^{1/2}$, more preferably at most 11 MPa$^{1/2}$. Further, said $R_{a,DEAA}$ for washing solvent a) may be at least 5 MPa$^{1/2}$, preferably at least 8 MPa$^{1/2}$, more preferably at least 10 MPa$^{1/2}$. For example, said $R_{a,DEAA}$ for monoethylene glycol (MEG) is 12 MPa$^{1/2}$. Further, preferably, said organic solvents for washing solvent a) have a $R_{a,heptane}$ which is greater than the $R_{a,DEAA}$ for the same solvent, wherein said difference in $R_{a,heptane}$ and $R_{a,DEAA}$ is at least 15 MPa$^{1/2}$, more preferably at least 16 MPa$^{1/2}$, most preferably at least 17 MPa$^{1/2}$. Further, preferably, said difference in $R_{a,heptane}$ and $R_{a,DEAA}$ is at most 25

$MPa^{1/2}$, more preferably at most 22 $MPa^{1/2}$, most preferably at most 20 $MPa^{1/2}$. For example, said difference in $R_{a,heptane}$ and $R_{a,DEAA}$ for monoethylene glycol is 16.3 $MPa^{1/2}$.

As mentioned above, the miscibilities, in heptane, of extraction solvent b) and washing solvent a) are preferably different in which case said solvents a) and b) are not identical. In specific, washing solvent a) may have a Hansen solubility parameter distance $R_{a,heptane}$ with respect to heptane as determined at 25° C. which is greater than such $R_{a,heptane}$ for extraction solvent b). Preferably, said difference in $R_{a,heptane}$ for solvents a) and b) is at least 1 $MPa^{1/2}$, more preferably at least 5 $MPa^{1/2}$, more preferably at least 10 $MPa^{1/2}$, more preferably at least 15 $MPa^{1/2}$, more preferably at least 20 $MPa^{1/2}$, more preferably at least 25 $MPa^{1/2}$. Further, preferably, said difference in $R_{a,heptane}$ for solvents a) and b) is at most 55 $MPa^{1/2}$, more preferably at most 50 $MPa^{1/2}$, more preferably at most 45 $MPa^{1/2}$, more preferably at most 40 $MPa^{1/2}$, more preferably at most 35 $MPa^{1/2}$, more preferably at most 30 $MPa^{1/2}$.

In specific, the washing solvent a) in step a) of the present process may comprise one or more solvents selected from the group consisting of water, ammonia and organic solvents selected from the group consisting of diols and triols, including monoethylene glycol (MEG), monopropylene glycol (MPG) and glycerol; glycol ethers, including oligoethylene glycols, including diethylene glycol, triethylene glycol and tetraethylene glycol, and polyethylene glycols (PEG) which may have a molecular weight of 200 to 1,000 g/mole or 200 to 700 g/mole; amides, including formamide and monoalkyl formamides and acetamides, wherein the alkyl group may contain 1 to 8 or 1 to 3 carbon atoms, including methyl formamide; dialkylsulfoxide, wherein the alkyl group may contain 1 to 8 or 1 to 3 carbon atoms, including dimethylsulfoxide (DMSO); sulfones, including sulfolane; hydroxy esters, including lactates, including methyl and ethyl lactate; aminic compounds, including ethylenediamine, monoethanolamine, diethanolamine and triethanolamine; carbonate compounds, including propylene carbonate and glycerol carbonate; and cycloalkanone compounds, including dihydrolevoglucosenone. Preferably, said washing solvent a) comprises one or more of water and above-mentioned diols and triols, in specific monoethylene glycol (MEG) and glycerol, and glycol ethers, in specific diethylene glycol, triethylene glycol, tetraethylene glycol and polyethylene glycols (PEG) which may have a molecular weight of 200 to 1,000 g/mole or 200 to 700 g/mole. More preferably, washing solvent a) comprises water, most preferably consists of water. In accordance with the present invention, washing solvent a) may comprise one or more solvents which are not mentioned above in combination with one or more solvents which are mentioned above, for example water, wherein the relative amount of the latter solvent(s) may vary within wide ranges and may be as low as for example 0.1 wt. % based on total washing solvent.

In step a), it may be preferred that the alkaline stream having a pH above 7 and comprising washing solvent a), for example water, has a pH of from 8 up to greater than 14, more preferably of from 8 to 14, more preferably of from 10 to 14, most preferably of from 12 to 14. In step a), a washing solvent a) containing stream having a pH above 7 may be provided by adding one or more salts selected from the group consisting of alkali metal carbonates and bicarbonates, including sodium bicarbonate, sodium carbonate, lithium carbonate, lithium bicarbonate, potassium carbonate and potassium bicarbonate, and alkali metal or alkaline earth metal hydroxides, including lithium hydroxide, sodium hydroxide, potassium hydroxide and calcium hydroxide, and ammonium hydroxide, to a washing solvent a) stream. Advantageously, using a washing solvent a) containing alkaline stream having such pH may result in removing heteroatom containing organic compounds and/or silicon containing compounds. Further, the washing performance of such alkaline stream may be improved by adding, to step a), a sorption agent as further described below with reference to sorption step (i).

Further, step a) may comprise two or more steps a) wherein in a first step a) an alkaline stream comprising washing solvent a) having a relatively low pH, for example of from 8 to 10, is fed, and in a second or subsequent step a) an alkaline stream comprising washing solvent a) having a relatively high pH, for example of from 10 to 14, is fed.

Still further, in step a), it may be preferred that the acid stream having a pH below 7 and comprising washing solvent a), for example water, has a pH of from lower than 1 to 6, more preferably of from 1 to 6, more preferably of from 2 to 5, most preferably of from 2 to 4. In step a), a washing solvent a) containing stream having a pH below 7 may be provided by adding an inorganic acid (mineral acid) or an organic acid to a washing solvent a) stream. Suitably, one or more inorganic acids selected from the group consisting of hydrochloric acid, nitric acid, phosphoric acid, boric acid, perchloric acid, hydrofluoric acid, hydroiodic acid and sulfuric acid may be added. And/or, suitably, one or more organic acids selected from the group consisting of sulfonic acids, including methane sulfonic acid and p-toluene sulfonic acid, and carboxylic acids, including formic acid, oxalic acid, acetic acid, lactic acid, uric acid, malic acid, tartaric acid and citric acid, may be added. Further, suitably, the acidity of the acid stream can be provided by an ion-exchange resin or ion-exchange polymer comprising an organic polymer, such as polystyrene sulfonate or polystyrene crosslinked with divinylbenzene, where the ion-exchange sites are introduced after polymerization by functionalization with an acid group, for example sulfonic or carboxylic acid groups.

Advantageously, using a washing solvent a) containing acid stream having such pH may result in removing heteroatom containing organic compounds and/or metals. Further, the washing performance of such acid stream may be improved by adding, to step a), a sorption agent as further described below with reference to sorption step (i). Especially, when a sorption agent (for example a clay) is also added, such sorption agent may at the same time advantageously be activated by the acid thereby further increasing the overall performance. In such case of "in situ" acid activation of a sorption agent, the pH of the stream comprising washing solvent a) is preferably below 6.5, more preferably of from 5.4 to 6.5.

Further, step a) may comprise two or more steps a), in specific two or more steps a1) or a2) as described above, wherein in a first step a) an acid stream comprising washing solvent a) having a relatively high pH, for example of from 4 to 6, is fed, and in a second or subsequent step a) an acid stream comprising washing solvent a) having a relatively low pH, for example of from 2 to 4, is fed.

Further, in addition to and separately from said alkaline and acid washing steps in step a) of the present process, a washing step using a stream comprising washing solvent a), for example water, and having a pH of about 7 ("neutral") may also be performed. The washing performance of such neutral stream may be improved by adding, to step a), a sorption agent as further described below with reference to sorption step (i).

In step a) of the present process, it may be preferred that the alkaline washing solvent a) containing stream having a pH above 7 as described above, is fed to a first step a), and a stream comprising washing solvent a), for example water, to be fed to a second or any other subsequent step a), preferably to the last step(s) a) before step b), has a pH of about 7. Such additional neutral washing step a) may also be considered as a rinsing step, in which step it is preferred not to add any sorption agent.

Further, in step a) of the present process, it may be preferred that the acid washing solvent a) containing stream having a pH below 7 as described above, is fed to a first step a), and a stream comprising washing solvent a), for example water, to be fed to a second or any other subsequent step a), preferably to the last step(s) a) before step b), has a pH of about 7. Such additional neutral washing step a) may also be considered as a rinsing step, in which step it is preferred not to add any sorption agent.

The temperature at which step a) is carried out may be in the range of from 4 to 400° C., more preferably in the range of from 4 to 300° C., most preferably in the range of from 4 to 200° C. In particular, preferably, said temperature is of from 30 to 200° C., more preferably 50 to 170° C., most preferably 60 to 150° C. The pressure at which step a) is carried out may be in the range of from atmospheric pressure to 100 bar, more preferably in the range of from atmospheric pressure to 20 bar, most preferably in the range of from atmospheric pressure to 6 bar. In particular, preferably, said pressure is of from greater than atmospheric pressure to 15 bar, preferably 1.1 to 10 bar, more preferably 1.5 to 8 bar, most preferably 2 to 6 bar.

Step a) may be performed continuously or batchwise, preferably continuously. Further, mixing in step a) may be performed in any way known to a skilled person. For example, a mixer may be used upstream of a phase separation apparatus as described below. Further, for example, in-line (or static) mixing may be performed upstream of such phase separation apparatus. Still further, mixing may be effected in an extraction column as described below.

Through such addition of washing solvent a) and mixing in step a), a first phase comprising washing solvent a), heteroatom containing organic compounds and optionally other contaminants and a second phase comprising aliphatic hydrocarbons, heteroatom containing organic compounds and optionally aromatic hydrocarbons result from step a), which phases may be separated into above-mentioned first stream and second stream, respectively. Thus, advantageously, said washing solvent a) as added in step a) separately from the liquid hydrocarbon feedstock stream, removes part of the heteroatom containing organic compounds and any other contaminants from the aliphatic hydrocarbons to be recovered, thereby at the same time preventing a build-up of such contaminants in a downstream part of the present process, and thus increasing the stability and reliability of the overall process.

The phase separation in step a) may be performed by any apparatus capable of separating two phases, including a decanter, a flotation device, a coalescer and a centrifuge, suitably a decanter. The phase separation in step a) may be carried out in a single stage, for example in a decanter, a flotation device, a coalescer or a centrifuge. For example, when using a decanter in step a), an upper phase comprising aliphatic hydrocarbons, heteroatom containing organic compounds and optionally aromatic hydrocarbons and a lower phase comprising washing solvent a), heteroatom containing compounds and optionally other contaminants may be separated into said second stream and first stream, respectively.

Further, step a) may be carried out in an extraction column comprising multiple separation stages. In the latter case, step a) comprises contacting at least part of the liquid hydrocarbon feedstock stream with washing solvent a) in the column and subjecting said feedstock stream to liquid-liquid extraction with the washing solvent a), resulting in a first stream comprising washing solvent a), heteroatom containing compounds and optionally other contaminants and a second stream comprising aliphatic hydrocarbons, heteroatom containing organic compounds and optionally aromatic hydrocarbons, wherein said washing solvent a) may be fed to the extraction column at a position which is higher than the position at which said feedstock stream is fed, thereby enabling a counterflow liquid-liquid extraction and resulting in a top stream from the extraction column (above "second stream") comprising aliphatic hydrocarbons, heteroatom containing organic compounds and optionally aromatic hydrocarbons and a bottom stream from the extraction column (above "first stream") comprising washing solvent a), heteroatom containing compounds and optionally other contaminants.

Internals in the above-mentioned extraction column contribute to the mixing of the feedstock stream and the washing solvent a). Such column internals are known in the art. The column internals may comprise a packing such as Raschig rings, Pall rings, Lessing rings, Bialecki rings, Dixon rings; sieving plates; or a random structured packing, among others, as described in Perry's Chemical Engineer's Handbook. Furthermore, the column may be provided with stirring means. For example, a shaft may run along the column and may be provided with rotors and stators fixed to the column.

Thus, advantageously, already in step a) before step b), any salts and/or silicon containing compounds and/or metals originating from the liquid hydrocarbon feedstock stream are removed, and part of the heteroatom containing organic compounds is also removed from the aliphatic hydrocarbons to be recovered from the liquid hydrocarbon feedstock stream, so that there is a reduced need to effect separation of such heteroatom containing organic compounds in subsequent extraction step b). Further, complications relating to such other contaminants, including salts and/or silicon containing compounds and/or metals originating from the liquid hydrocarbon feedstock stream, such complications being discussed in the introduction of this specification, may advantageously also be avoided by already removing such other contaminants in a first step. Thus, not only may the efficiency of extraction step b) be improved, but at the same time, such complications caused by such contaminants (heteroatom containing organic compounds and any other contaminants) may advantageously be prevented and thus the stability and reliability of the overall process may be increased.

At least part of the first stream comprising washing solvent a), heteroatom containing compounds and optionally other contaminants resulting from step a) may be recycled to step a), whereas another part may be bled from the process. The heteroatom containing organic compounds removed in step a) may be converted into fuel, optionally after a hydrotreatment to remove the heteroatoms. Further, said compounds removed in step a) may be further separated into various fractions which may be used as solvents.

In a case wherein step a) comprises a neutral washing step in addition to the acid and alkaline washing steps, the multiple steps in series in step a) may be performed such that in a first step a) at least part of the liquid hydrocarbon feedstock stream is mixed with washing solvent a), wherein a stream comprising washing solvent a) to be added has a pH below 7 (acid) as described above, and, optionally after removing any sorption agent as further described below with reference to sorption step (i), the resulting liquid phases may be separated in a decanter, a flotation device, a coalescer and a centrifuge, suitably a decanter, as described above, resulting in a first stream comprising washing solvent a), heteroatom containing compounds and optionally other contaminants and a second stream comprising aliphatic hydrocarbons, heteroatom containing organic compounds, optionally other contaminants and optionally aromatic hydrocarbons, and in a second step a) said first step a) is repeated but using a stream comprising washing solvent a) having a pH above 7 (alkaline) as described above instead, and at least part of the second stream resulting from the second step a) is contacted, in a third step a), with a washing solvent a) stream having a pH of about 7 as described above, for example in an extraction column as described above, and said second stream may be subjected to liquid-liquid extraction with washing solvent a), resulting in a first stream comprising washing solvent a), heteroatom containing compounds and optionally other contaminants and a second stream comprising aliphatic hydrocarbons, heteroatom containing organic compounds and optionally aromatic hydrocarbons, and wherein at least part of the second stream resulting from the third step a) may be fed to step b). Optionally, said first stream, in specific the first stream resulting from said first step a) and/or said second step a), may comprise any sorption agent as further described below with reference to sorption step (i), in case said sorption agent is not removed before separation of the first and second streams in said first step a) and/or second step a). In the latter case, the sorption agent may be removed from said first stream, for example by filtration.

In the present invention, washing step a) may comprise one or more of the following sequences of washing steps:
1) an acid washing step as described above, followed by an alkaline washing step as described above, optionally followed by a neutral washing step (or rinsing step) as described above;
2) an acid washing step as described above, optionally followed by a neutral washing step as described above, followed by an alkaline washing step as described above, optionally followed by a neutral washing step as described above;
3) an alkaline washing step at a relatively low pH as described above, followed by an alkaline washing step at a relatively high pH as described above, optionally followed by a neutral washing step as described above, followed by an acid washing step as described above, optionally followed by a neutral washing step as described above.

Step b)—Extraction with Extraction Solvent b)

In step b) of the present process, at least part of the second stream resulting from step a), comprising aliphatic hydrocarbons, heteroatom containing organic compounds and optionally aromatic hydrocarbons, from which part of the heteroatom containing organic compounds and any other contaminants are removed by contacting at least part of that stream with washing solvent a) in preceding step a), is contacted with an extraction solvent b) which contains one or more heteroatoms, and that stream is subjected to liquid-liquid extraction with extraction solvent b), resulting in a first stream comprising aliphatic hydrocarbons and optionally heteroatom containing organic compounds and a second stream comprising extraction solvent b), heteroatom containing organic compounds and optionally aromatic hydrocarbons.

In step b) of the present process, the second stream resulting from step a) may be fed to a column (extraction column). Further, a solvent stream which comprises the extraction solvent b) may be fed to the column at a position which is higher than the position at which the second stream resulting from step a) is fed, thereby enabling a counterflow liquid-liquid extraction and resulting in a top stream from the column (above "first stream") comprising aliphatic hydrocarbons and optionally heteroatom containing organic compounds and a bottom stream from the column (above "second stream") comprising extraction solvent b), heteroatom containing organic compounds and optionally aromatic hydrocarbons.

In step b), the weight ratio of the extraction solvent b) to the second stream resulting from step a) may be at least 0.05:1 or at least 0.2:1 or at least 0.5:1 or at least 1:1 or at least 2:1 or at least 3:1 and may be at most 5:1 or at most 3:1 or at most 2:1 or at most 1:1. Further, the temperature in step b) may be at least 0° C. or at least 20° C. or at least 30° C. or at least 40° C. or at least 50° C. and may be at most 200° C. or at most 150° C. or at most 100° C. or at most 70° C. or at most 60° C. or at most 50° C. or at most 40° C. The pressure in step b) may be at least 100 mbara or at least 500 mbara or at least 1 bara or at least 1.5 bara or at least 2 bara and may be at most 50 bara or at most 30 bara or at most 20 bara or at most 15 bara or at most 10 bara or at most 5 bara or at most 3 bara or at most 2 bara or at most 1.5 bara. The temperature and pressure in step b) are preferably such that both the hydrocarbons from the second stream resulting from step a) and the extraction solvent b) are in the liquid state.

In step b), aliphatic hydrocarbons are recovered by liquid-liquid extraction of heteroatom containing organic compounds and optionally aromatic hydrocarbons with extraction solvent b). Further, preferably, the recovered aliphatic hydrocarbons comprise aliphatic hydrocarbons having a boiling point of from 30 to 300° C. and aliphatic hydrocarbons having a boiling point of from greater than 300 to 600° C. in a weight ratio of from 99:1 to 1:99. The above description of the weight ratio of aliphatic hydrocarbons having a boiling point of from 30 to 300° C. to aliphatic hydrocarbons having a boiling point of from greater than 300 to 600° C. in relation to aliphatic hydrocarbons in the liquid hydrocarbon feedstock stream also applies to the recovered aliphatic hydrocarbons.

In step b), said liquid-liquid extraction results in a first stream comprising aliphatic hydrocarbons and optionally heteroatom containing organic compounds and a second stream comprising extraction solvent b), heteroatom containing organic compounds and optionally aromatic hydrocarbons. Within the present specification, the former stream (first stream) comprising recovered aliphatic hydrocarbons may also be referred to as a "raffinate stream" and the latter stream (second stream) may also be referred to as an "extract stream". Such raffinate stream has a reduced content of aromatic hydrocarbons, conjugated aliphatic compounds having two or more carbon-carbon double bonds, and heteroatom containing organic compounds. Such raffinate stream comprises no or at most 10 wt. % or at most 5 wt. % or at most 1 wt. % or substantially no aromatic hydrocarbons. Further, such raffinate stream comprises no or at most 15 wt. % or at most 10 wt. % or at most 5 wt. % or at most 1 wt. % or substantially no conjugated aliphatic compounds having two or more carbon-carbon double bonds. Further, such raffinate stream comprises no or at most 1 wt. % or substantially no heteroatom containing organic compounds.

The extraction solvent b) used in step b) of the present process, which may be fed as a solvent stream to a column in step b), preferably has a density which is at least 3% or at least 5% or at least 8% or at least 10% or at least 15% or at least 20% higher than the density of the second stream resulting from step a). Further, said density may be at most 50% or at most 40% or at most 35% or at most 30% higher than the density of the second stream resulting from step a).

Further, the extraction solvent b) used in step b) contains one or more heteroatoms, which may be oxygen, nitrogen and/or sulfur. Still further, it is preferred that said extraction solvent b) is thermally stable at a temperature of 200° C. Still further, said extraction solvent b) may have a boiling point which is at least 50° C. or at least 80° C. or at least 100° C. or at least 120° C. and at most 300° C. or at most 200° C. or at most 150° C. Still further, it is preferred that said extraction solvent b) has no or a relatively low miscibility in heptane. Preferably, extraction solvent b) has such miscibility in heptane that at most 30 wt. % or at most 20 wt. % or at most 10 wt. % or at most 3 wt. % or at most 1 wt. % of extraction solvent b), based on weight of heptane, is miscible in heptane. The miscibility of a certain compound in another compound, such as heptane, may be determined by any general method known to a skilled person in the art, including ASTM method D1476. Where in the present specification reference is made to the miscibility of a compound in another compound, this means miscibility at 25° C.

Further, the extraction solvent b) in step b) may have a Hansen solubility parameter distance $R_{a,heptane}$ with respect to heptane as determined at 25° C. of at least 3 MPa$^{1/2}$, preferably at least 5 MPa$^{1/2}$, more preferably at least 10 MPa$^{1/2}$ more preferably at least 15 MPa$^{1/2}$. Further, said $R_{a,heptane}$ for extraction solvent b) may be lower than 45 MPa$^{1/2}$ or at most 40 MPa$^{1/2}$, preferably at most 35 MPa$^{1/2}$, more preferably at most 30 MPa$^{1/2}$, more preferably at most 25 MPa$^{1/2}$ For example, said $R_{a,heptane}$ for N-methylpyrrolidone (NMP) is 15 MPa$^{1/2}$.

Still further, said extraction solvent b) may have a difference in Hansen solubility parameter distance $R_{a,heptane}$ with respect to heptane compared to Hansen solubility parameter distance $R_{a,toluene}$ with respect to toluene (i.e. $R_{a,heptane} - R_{a,toluene}$) as determined at 25° C. of at least 1.5 MPa$^{1/2}$, preferably at least 2 MPa$^{1/2}$. Further, said difference in $R_{a,heptane}$ compared to $R_{a,toluene}$ for extraction solvent b) may be at most 4.5 MPa$^{1/2}$, preferably at most 4 MPa$^{1/2}$.

Hansen solubility parameters (HSP) can be used as a means for predicting the likeliness of one component compared to another component. More specifically, each component is characterized by three Hansen parameters, each generally expressed in MPa$^{0.5}$: $\delta_d$, denoting the energy from dispersion forces between molecules; $\delta_p$, denoting the energy from dipolar intermolecular forces between molecules; and $\delta_h$, denoting the energy from hydrogen bonds between molecules. The affinity between compounds can be described using a multidimensional vector that quantifies these solvent atomic and molecular interactions, as a Hansen solubility parameter (HSP) distance $R_a$ which is defined in Equation (1):

$$(R_a)^2 = 4(\delta_{d2}-\delta_{d1})^2 + (\delta_{p2}-\delta_{p1})^2 + (\delta_{h2}-\delta_{h1})^2 \quad (1)$$

wherein
$R_a$=distance in HSP space between compound 1 and compound 2 (MPa$^{0.5}$)
$\delta_{d1}$, $\delta_{p1}$, $\delta_{h1}$=Hansen (or equivalent) parameter for compound 1 (in MPa$^{0.5}$)
$\delta_{d2}$, $\delta_{p2}$, $\delta_{h2}$=Hansen (or equivalent) parameter for compound 2 (in MPa$^{0.5}$)

Thus, the smaller the value for $R_a$ for a given solvent calculated with respect to the compound to be recovered (i.e., the compound to be recovered being compound 1 and the solvent being compound 2, or vice versa), the higher the affinity of this solvent for the compound to be recovered will be.

Hansen solubility parameters for numerous solvents can be found in, among others, *CRC Handbook of Solubility Parameters and Other Cohesion Parameters*, Second Edition by Allan F. M. Barton, CRC press 1991; *Hansen Solubility Parameters: A User's Handbook* by Charles M. Hansen, CRC press 2007.

In specific, the extraction solvent b) used in step b) of the present process may comprise ammonia or, preferably, one or more organic solvents selected from the group consisting of diols and triols, including monoethylene glycol (MEG), monopropylene glycol (MPG), any isomer of butanediol and glycerol; glycol ethers, including oligoethylene glycols, including diethylene glycol, triethylene glycol and tetraethylene glycol, and monoalkyl ethers thereof, including diethylene glycol ethyl ether; amides, including N-alkylpyrrolidone, wherein the alkyl group may contain 1 to 8 or 1 to 3 carbon atoms, including N-methylpyrrolidone (NMP), formamide and di- and monoalkyl formamides and acetamides, wherein the alkyl group may contain 1 to 8 or 1 to 3 carbon atoms, including dimethyl formamide (DMF), methyl formamide and dimethyl acetamide; dialkylsulfoxide, wherein the alkyl group may contain 1 to 8 or 1 to 3 carbon atoms, including dimethylsulfoxide (DMSO); sulfones, including sulfolane; N-formyl morpholine (NFM); furan ring containing components and derivatives thereof, including furfural, 2-methyl-furan, furfuryl alcohol and tetrahydrofurfuryl alcohol; hydroxy esters, including lactates, including methyl and ethyl lactate; trialkyl phosphates, including triethyl phosphate; phenolic compounds, including phenol and guaiacol; benzyl alcoholic compounds, including benzyl alcohol; aminic compounds, including ethylenediamine, monoethanolamine, diethanolamine and triethanolamine; nitrile compounds, including acetonitrile and propionitrile; trioxane compounds, including 1,3,5-trioxane; carbonate compounds, including propylene carbonate and glycerol carbonate; and cycloalkanone compounds, including dihydrolevoglucosenone.

More preferably, said extraction solvent b) comprises one or more of above-mentioned dialkylsulfoxide, in specific DMSO; sulfones, in specific sulfolane; above-mentioned N-alkylpyrrolidone, in specific NMP; and a furan ring containing component, in specific furfural. Even more preferably, said extraction solvent b) comprises one or more of above-mentioned N-alkylpyrrolidone, in specific NMP, and a furan ring containing component, in specific furfural. Most preferably, extraction solvent b) comprises NMP.

An aqueous solution of a quaternary ammonium salt, in specific trioctyl methyl ammonium chloride or methyl tributyl ammonium chloride, may also be used as the extraction solvent b) in step b).

As mentioned above, the second stream resulting from step b), which stream for the above-mentioned first (extraction) column corresponds with the bottom stream from such column, comprises extraction solvent b), heteroatom containing organic compounds and optionally aromatic hydrocarbons. Said stream may additionally comprise conjugated aliphatic compounds having two or more carbon-carbon double bonds in a case wherein such compounds are present in the second stream resulting from step a).

In the present invention, extraction solvent b) may be recovered from the second stream resulting from step b), and optionally from the first stream resulting from step b) in case the latter stream also comprises extraction solvent b), and then advantageously recycled to step b). Suitably, said extraction solvent may be recovered and recycled in any way, for example in a way as described in WO2020212315 or in co-pending patent application no. EP20202249.7 filed on 16 Oct. 2020, the disclosures of which are herein incorporated by reference.

Advantageously, any aromatic hydrocarbons and conjugated aliphatic compounds having two or more carbon-carbon double bonds removed when recovering extraction solvent b) as described above, may be blended with pygas and processed into fuel or used in the production of aromatic compounds. Likewise, the heteroatom containing organic compounds removed in such recovery may also be converted into fuel, optionally after a hydrotreatment to remove the heteroatoms. Further, said compounds removed in such recovery may be further separated into various fractions which may be used as a solvent.

Optional Sorption Steps (i), (ii), (iii) and (iv)

Optionally, in the present process, one or more of the following sorption steps (i), (ii), (iii) and (iv) may be performed. In specific, optionally:
(i) during step a), at least part of the liquid hydrocarbon feedstock stream is contacted with a sorption agent before the first and second streams are separated in step a); and/or
(ii) between a preceding step a) and a subsequent step a), at least part of the second stream resulting from the preceding step a) is contacted with a sorption agent; and/or
(iii) between steps a) and b), at least part of the second stream resulting from step a) is contacted with a sorption agent; and/or
(iv) the first stream resulting from step b) comprises aliphatic hydrocarbons and heteroatom containing organic compounds and, after step b), at least part of that stream is contacted with a sorption agent.

In the present invention, advantageously, a sorption agent may be used in steps (i), (ii), (iii) and (iv) to remove heteroatom containing organic compounds and optionally aromatic hydrocarbons, and optionally other contaminants such as the above-mentioned silicon containing compounds and metals, which contaminants are in the liquid hydrocarbon feedstock stream or which may not be completely removed in extraction step b) but which are entrained in the first stream resulting from step a) which comprises the aliphatic hydrocarbons to be recovered, for example because of a relatively high concentration of these contaminants in the liquid hydrocarbon feedstock stream. By such sorption, advantageously, a final purified hydrocarbon product may be obtained which is of sufficiently high quality so that it may be further processed, for example be fed into a steam cracker.

Further, as discussed above, the extracted heteroatom containing organic compounds and optionally said other contaminants in the second (extract) stream resulting from step b), comprising extraction solvent b), heteroatom containing organic compounds and optionally aromatic hydrocarbons, may build up in any recycle extraction solvent b) stream to said step b). Said heteroatom containing organic compounds that cause such build up, may comprise the components with the highest polarity of all the heteroatom containing organic compounds as extracted in step b) of the present process. In such case, advantageously, by optional sorption step (iv) after extraction step b), in the process of the present invention, a relatively pure final hydrocarbon product, that is substantially free of heteroatom containing organic compounds and optionally other contaminants, can then still be delivered and for example be fed into a steam cracker. Further, in addition, through washing step a), and through optional sorption step (i) during washing step a) and/or optional sorption step (ii) between multiple washing steps a) and/or optional sorption step (iii) after washing step a) and before extraction step b), part of these heteroatom containing organic compounds and other optional contaminants are already removed from the feedstock stream before being subjected to extraction step b), thereby preventing said build-up in any extraction solvent b) recycle stream. A relatively pure extraction solvent b) stream can then advantageously be recycled to step b) and used to extract further heteroatom containing organic compounds and optional aromatic hydrocarbons from fresh feed. Thus, in the present invention, the above-mentioned contaminants, including heteroatom containing organic compounds and any other contaminants, including any salts, that build up or could build up as discussed above, may advantageously already be removed in washing step a) which precedes extraction step b) and be concentrated into the sorption agent as used in said optional sorption steps (i), (ii), (iii) and/or (iv), thereby preventing a build-up of such contaminants in any recycle stream in the present process and eventually resulting in a relatively pure final hydrocarbon product.

Because of the combination of (i) the above-described pre-washing step a) and (ii) the above-described optional use of a sorption agent before and/or after extraction step b), in the present invention there may be no need or a substantially reduced need to apply other, cumbersome methods for mitigating a build-up of these contaminants. For example, there may be no need or a substantially reduced need to bleed part of any recycle stream (e.g. any recycle extraction solvent b) stream) before recycling, wherein either (i) such bleed stream is discarded resulting in a loss of extraction solvent or (ii) the extraction solvent may be recovered from such bleed stream, for example by distillation thereof, which is however cumbersome.

It is envisaged that the removal of heteroatom containing organic compounds, optionally aromatic hydrocarbons and optionally other contaminants as described above, by the above-mentioned sorption is applied in the present process in one or more of above optional sorption steps (i), (ii), (iii) and (iv).

Accordingly, in specific, the above-mentioned sorption may be applied in the present process in one or more of the following optional sorption steps (i), (ii), (iii) and (iv), corresponding with above optional sorption steps (i), (ii), (iii) and (iv), wherein:
(i) part of the heteroatom containing organic compounds is removed from the liquid hydrocarbon feedstock stream by contacting at least part of that stream with a sorption agent during step a) before the first and second streams are separated in step a), and at least part of the treated stream resulting from step (i) is fed to step b); and/or
(ii) part of the heteroatom containing organic compounds is removed from the second stream resulting from a preceding step a) by contacting at least part of that stream with a sorption agent, and at least part of the treated stream resulting from step (ii) is fed to a subsequent step a); and/or
(iii) part of the heteroatom containing organic compounds is removed from the second stream resulting from step a) by contacting at least part of that stream with a sorption agent, and at least part of the treated stream resulting from step (iii) is fed to step b); and/or (iv) the first stream resulting from step b) comprises aliphatic hydrocarbons and heteroatom containing organic compounds, and heteroatom containing organic compounds are removed from that stream by contacting at least part of that stream with a sorption agent.

Preferably, if in the present process a sorption step is performed, the above-mentioned sorption is applied in the present process in one or more of said steps (i), (iii) and (iv). Further, in case sorption step (iii) is applied, then at least part of the second stream resulting from the last step a) in series may be contacted with a sorption agent.

In case the present process comprises one sorption step, such single sorption step is preferably sorption step (iii) or (iv), most preferably sorption step (iv). In case the present process comprises two sorption steps, these are preferably sorption steps (i) and (iii) or sorption steps (i) and (iv), most preferably sorption steps (i) and (iv).

By optional sorption steps (i), (ii), (iii) and (iv), at least part of the contaminants will advantageously be concentrated into the sorption agent(s) as used in such sorption step(s), in addition to the removal by means of extraction step b) of the present process, thereby making it possible that a final hydrocarbon product of sufficiently high quality (purity) can still be delivered. Optional sorption steps (i), (ii), (iii) and (iv) make it possible that with the present process, liquid hydrocarbon feedstock streams containing a relatively high amount of heteroatom containing organic contaminants and optionally other contaminants may still be processed. In addition, a build-up of these contaminants in any extraction solvent b) recycle stream to step b) would, advantageously, not result in a build-up of these contaminants in the final hydrocarbon product through sorption step (iv) in the present process. Further, in addition, through sorption steps (i), (ii) and (iii) in the present process in which latter steps part of these contaminants is already removed from the feedstock stream before being subjected to extraction step b), said build-up of these contaminants in any extraction solvent b) recycle stream to step b) may be prevented. Thus, the sorption agent retains contaminants, which sorption agent may eventually be regenerated or be removed from the process and replaced by fresh sorption agent, thereby continuing to provide the above-described advantages.

Still further, in the present invention, part of the treated streams resulting from optional sorption steps (i), (ii) and (iii) of the present process may be fed to extraction step b), whereas another part may by-pass said step b). It is also envisaged, which is not in accordance with the present invention as claimed, that the entire treated streams resulting from steps (i), (ii) and (iii) may by-pass step b). For example, such by-pass may be suitable in case the quality of said treated stream is sufficiently high such that it is already within the specifications of a steam cracker feed. At least part of said treated stream may then suitably be fed directly to a steam cracker, without an extraction step in between.

Advantageously, through optional sorption steps (i), (ii), (iii) and/or (iv) in combination with washing step a), and the option of a (partial) by-pass of extraction step b) as described above, flexibility is added to the present process such that a wide range of liquid hydrocarbon feedstocks having different qualities (different contaminants and/or different levels of contaminants) can be treated.

In above-mentioned sorption steps (i), (ii), (iii) and (iv), the contacting with the sorption agent may be carried out in any way known to a skilled person.

In sorption step (i), it is preferred that the sorption agent is present in step a) as a suspension comprising sorption agent particles. Such sorption agent particles may be added to a stream comprising washing solvent a) to be added to step a). In the case of such suspension, it is preferred that the sorption agent is removed from the treated stream before the first and second streams are separated in step a), for example by filtration. Alternatively, the sorption agent may be removed together with the first stream comprising washing solvent a) and heteroatom containing compounds, by settling or by applying a different method, for example by using a separator such as a centrifuge or a hydrocyclone, when separating the first and second streams in step a).

Further, in sorption steps (ii), (iii) and (iv), the sorption agent may be present as a suspension comprising sorption agent particles as described above for sorption step (i), or may be fixed in a packed bed. Preferably, in sorption steps (ii), (iii) and (iv), the sorption agent is fixed in a packed bed.

In the present invention, the relative amount of the sorption agent in sorption steps (i), (ii), (iii) and (iv) in case the above-mentioned suspension is used, may be of from 0.01 wt. % to 20 wt. %, preferably 0.1 wt. % to 5 wt. %, more preferably 0.1 wt. % to 1 wt. %, based on the to be treated feed to the sorption step. Further, in case the above-mentioned packed bed is used in sorption steps (ii), (iii) and (iv), the Liquid Hourly Space Velocity (LHSV) may be of from 0.1 to 50 1/h, preferably 1 to 10 1/h. A certain target LHSV may depend on a number of factors, such as temperature and concentration of the contaminants.

In the present specification, sorption means a process in which one substance (the sorption agent) takes up or holds another substance by absorption, adsorption or a combination of both. Preferably, the sorption agent used in the present invention is a sorption agent, which preferentially sorbs heteroatom containing compounds, optionally aromatic hydrocarbons and optionally other contaminants as described above. In specific, it is preferred that heteroatom containing compounds, optionally aromatic hydrocarbons and optionally other contaminants as described above are preferentially sorbed as compared to aliphatic hydrocarbons to be recovered and as compared to any extraction solvent and/or washing solvent as defined in the present specification.

Sorption agents for use in steps (i), (ii), (iii) and (iv) of the present process suitably have a porous structure comprised of micro-, meso- or macropores or a combination thereof. According to IUPAC notation, microporous structures have pore diameters of less than 2 nm (20 Å, angstroms), mesoporous structures have pore diameters between 2 and 50 nm (20-500 Å), and macroporous structures have pore diameters greater than 50 nm (500 Å).

Sorption agents which may suitably be used in steps (i), (ii), (iii) and (iv) are not limited to the specific materials listed in the present specification. In general, any material characterized by having a relatively high specific surface area, a porous structure comprising micro-, meso- or macropores or a combination thereof, from natural origin or synthetic, from a mineral or an organic source, with a treated or untreated surface, and in any form may be used in this invention. Said specific surface area may be in the range of from 1 to 3000 m$^2$/g, preferably 50 to 2000 m$^2$/g, more preferably 100 to 1000 m$^2$/g. Said specific surface area may be at least 1 m$^2$/g or at least 10 m$^2$/g or at least 50 m$^2$/g. Further, it may be at most 3000 m$^2$/g or at most 1000 m$^2$/g or at most 500 m²/g. Furthermore, suitable sorption agents for use in steps (i), (ii), (iii) and (iv) have a pore volume of at least 0.001 cm³/g or at least 0.01 cm³/g or at least 0.1 cm³/g, and at most 1 cm³/g or at most 3 cm³/g or at most 5 cm³/g or at most 10 cm³/g. Suitable sorption agents for use in steps (i), (ii), (iii) and (iv) may fulfill two from the above-mentioned characteristics, namely pore size and surface area, or pore size and pore volume, or surface area and pore volume.

Sorption agents that may be conveniently used in steps (i), (ii), (iii) and (iv) of the process of the present invention may be synthetic or natural molecular sieves. Further, sorption agents that may be conveniently used in steps (i), (ii), (iii) and (iv) of the process of the present invention may be molecular sieves of inorganic origin, such as metal oxides wherein the metal is one or more of alkaline earth, transition and post-transition metals, such as Al, Si, Zn, Mg, Ti, Zr, or zeolites, clays, activated clays, alumina, activated alumina, amorphous alumina, silica gels, diatomaceous earth, magnesium silicates, aluminum silicates, amorphous silica, porous glass and the like; or may be molecular sieves of organic origin, such as activated carbon, cross-linked and porous polymers, carbonaceous materials, such as carbon char ("char" stands for "charcoal"), graphene-based nanomaterials and single-wall or multi-wall carbon nanotubes; or may be hybrid molecular sieves, such as metal-organic frameworks. The sorption agent may be dispersed in a porous amorphous inorganic or organic matrix (also referred to as binder material), having channels and cavities therein that enable liquid access to the sorption agent. Alternatively, the sorption agent may be used without a binder material.

The sorption agent(s) used in steps (i), (ii), (iii) and (iv) of the present process may be one or more sorption agents selected from the group consisting of bleaching clays, hydrogel silica, silicates and activated carbon. Bleaching clays are especially preferred.

Bleaching clay minerals are hydrous phyllosilicates that can include variable amounts of aluminum, iron, magnesium, alkali metals, alkaline earths and other cations. Phyllosilicates may comprise the following subgroups of minerals: serpentine, clay minerals, mica and chlorite.

Preferably, sorbents suitable for this invention are phyllosilicates from the serpentine-kaolin group, the talc-pyrophillite group, the smectite group, the vermiculite or illite group, and/or the mica group. The phyllosilicates of the serpentine group may comprise antigorite, chrysotile and lizardite. The phyllosilicates of the kaolin group may comprise halloysite, kaolinite, illite, montmorillonite, vermiculite, talc, sepiolite, palygorskite (or attapulgite), and pyrophyllite. The phyllosilicates of the mica group may comprise biotite, fuchsite, muscovite, phlogopite, lepidolite, margarite, glauconite. The phyllosilicates of the chlorite group may comprise chlorite.

More preferably, suitable sorbents for this invention include highly active clays from the smectite group such as bentonite, which may contain mostly montmorillonite, or sepiolite, which clays may be applied after acid activation; naturally active, also called Fuller's Earth; and surface modified sorbents which may be activated "in-situ" by addition of an acid, such as hormite, attapulgite (or palygorskite) and sepiolite. Those clays may also contain some other minerals such as calcium carbonate, quartz, and feldspar. Suitable examples of commercially available bleaching clays are Grade F series and Nevergreen from BASF; Pure-Flo series and Perform series from Oil-Dri Corp; CynerSorb series from Imerys; and the Tonsil series from Clariant.

Other materials that could be used as suitable sorbents in steps (i), (ii), (iii) and (iv) of this invention are hydrated layered alkali silicates. Those can be natural or synthetic and comprise $SiO_2$ layers (sheets) provided with a negative charge, with alkali cations for charge compensation and, in some cases, water between the layers. Examples of hydrated layered silicate are kanemite, octosilicate, magdiite and kenyaite. Furthermore, hydrated layered alkali silicates can be functionalized resulting in inorganic-organic hybrids with sorption purpose. Hydrated layered alkali silicates are preferably used for the removal of metal ions because of their high cation exchange capacity. Ion exchange resins also have the ability to replace mineral acids where used as catalyst and to remove contaminants such as metals and heteroatom containing compounds, including phenols, aldehydes and organic acids. For instance, they have been used for the removal of fatty acids from oils. Commercially available ion exchange resins are those from the Amberlite™ series from Dow-Dupont, including Amberlyst A23 (for acid removal), Amberlite XAD4 (for phenol removal), Amberlyst series (instead of mineral acid in a reaction). Such ion exchange resins may also suitably be used as sorption agent in the present invention.

Clays or layered silicate sorbents suitable for use in steps (i), (ii), (iii) and (iv) of this invention may be characterized by their pore volume, surface area, ion exchange capacity (IEC) and pore size distribution. Clays or layered silicates suitable for this invention have pore volume of at least 0.1 cm³/g, more preferably greater than 0.4 cm³/g, and most preferably greater than 0.5 cm³/g. The specific pore volume is preferably up to 1.0 cm³/g, more preferably up to 0.8 cm³/g and most preferably up to 0.7 cm³/g. Clays or layered silicates suitable for this invention have surface areas preferably in the range from 100 m²/g to 500 m²/g, more preferably from 200 m²/g to 400 m²/g. Suitable layered silicates for this invention have ion exchange capacity (IEC) of at least 25 meq/100 g but preferably above 40 meq/100 g and most preferably in the range from 50 meq/100 g to 80 meq/100 g. Synthetic layered silicates may have ion exchange capacities up to 500 meq/100 g. Clays or layered silicates suitable for this invention are characterized for having a pore size distribution such as preferably at least 20%, more preferably at least 22% and most preferably at least 30% of the total pore volume is provided by pores with a diameter of at most 7.5 nm. Preferably at least 40%, more preferably at least 45%, most preferably at least 50% of the total pore volume is provided by pores with a diameter of at most 14 nm. Preferably less than 40%, more preferably less than 35% of the total pore volume is provided by pores with a diameter of more than 25 nm.

Furthermore, the sorbent used in steps (i), (ii), (iii) and (iv) of this invention may be a combination of sorbents disclosed in this specification. Example of clay combinations are attapulgite/montmorillonite mixtures which contain preferably 10-90 wt. % of attapulgite, more preferably 20-60 wt. % of attapulgite and most preferably 30-50 wt. % of attapulgite.

The above-mentioned inorganic sorbents may first need to be subjected to a treatment or activation, thermal or chemical, as is known to the skilled person, so as to optimally remove contaminants in steps (i), (ii), (iii) and (iv).

Sorption agents comprising carbon such as activated carbon and carbon char, suitable for use in steps (i), (ii), (iii) and (iv) of this invention, may consist mainly of carbon, for example, a substance comprising 80 to 100 wt. % of carbon, preferably 90 to 100 wt. % of carbon, more preferably 95 to 100 wt. %, most preferably 98 to 100 wt. % of carbon, and highly preferably 99 to 100 wt. % of carbon.

A preferred activated carbon as sorption agent for removing one or more of the above-mentioned contaminants, including heteroatom containing organic compounds, in steps (i), (ii), (iii) and (iv), is from a bituminous source. Further, an activated carbon which may be used as such sorption agent is preferably characterized by having an iodine number in the range from 500 to 1200 mg/g; and a high molasses number in the range from 95 to 1500, and preferably, in the range from 200 to 1500. "Iodine number" is a relative measure of pores at sizes of 10 to 28 Angstroms. It is reported in milligrams of elemental iodine sorbed per gram of granulated activated carbon and determines the area available on the activated carbon to sorb low molecular weight organic compounds. Iodine number may be determined according to ASTM D4607. "Molasses number" measures the degree to which an activated carbon removes color from a stock solution. It measures the pores greater than 28 Angstroms. These are the pores responsible for removing larger molecular weight organic compounds. In this case, the amount of sorbed molasses is quantified.

Furthermore, suitable activated carbons for this invention have a total specific surface area in the range of from 600 to 2000 $m^2/g$ and a total pore volume in the range of from 0.9 to 2.5 ml/g. Still further, a preferred activated carbon for this invention has a specific surface area above 100 $m^2/g$ and a pore volume above 0.5 ml/g, for pores larger than 20 Angstroms. These properties are advantageous in removing relatively large molecules comprising said heteroatom containing organic compounds and optional aromatic hydrocarbons to be removed in steps (i), (ii), (iii) and (iv).

Activated carbons and carbon chars, of which the surfaces are modified and/or functionalized, may also suitably be used in steps (i), (ii), (iii) and (iv). Suitable methods to produce functional properties on carbon material surfaces include oxidation by liquid and gaseous oxidants, grafting of functional groups onto the material surfaces, physisorption of ligands, vapor deposition, and/or functional groups developed during carbon activation processes.

Suitable sorbents for steps (ii), (iii) and (iv) of the present invention can be molecular sieves which are zeolite-based, silica gel, alumina, clay-based or activated carbon.

In the present invention, a subgroup of heteroatom containing organic compounds to be removed in sorption steps (ii), (iii) and (iv) may comprise organochlorides which can be polar or non-polar. A sorption agent that comprises a zeolite is suitable for such organochloride removal. In specific, a sorption agent that comprises a zeolite which comprises Faujasite (FAU) framework such as X and Y, dealuminated zeolite Y, low sodium Ultrastable Y (USY); MFI-type such as ZSM-5 and Pentasil Zeolite; MWW-type such as MCM-22, ITQ-1, SSZ-25; BEA-type such as zeolite beta; and Mordenite (MOR) type, is suitable as sorption agent in the present invention, especially for organochloride removal. Furthermore, the zeolite component of the sorption agent may be impregnated with a metal cation derived from an alkali metal, an alkaline earth metal, a transition metal or a post-transition metal as defined in the Periodic Table of Elements. Because organochlorides can release the chloride in the form of hydrochloric acid after interacting with the zeolite-based sorbent, the sorption agent may need to be also provided with a basic or amphoteric oxide, such as an alkali metal or earth alkaline metal oxide, hydroxide or carbonate, or an activated alumina or another metal oxide that can capture the released hydrochloric acid. Examples of commercially available zeolite-based materials suitable for this invention are adsorbents PCL-100 from UOP, CL-850 from BASF and TCR-16 from UniCat.

Further, in the present invention, another subgroup of heteroatom containing organic compounds to be removed in sorption steps (ii), (iii) and (iv) may comprise polar components. Sorption agents that comprise silica gel are suitable for removing such polar components. A suitable example of a commercially available silica gel for removal of polar components is TRISYL® from Grace Materials Technologies. Furthermore, a suitable sorption agent for preferential sorption of polar components, including above-mentioned organochlorides, comprises a zeolite-based material with a polarity as determined by its Si/Al ratio, or a zeolite that has undergone treatment, such as cation exchange or surface modification, to increase its affinity for the heteroatom containing compounds and preferentially polar compounds.

In the present invention, possible contaminants that may have to be removed by the sorption agent, may be the above-mentioned silicon containing compounds, such as silica and siloxane compounds. Preferably, sorption agents which comprise silica gel, zeolite 13X, activated alumina, hydrotalcite (a layered double hydroxide clay of general formula $Mg_6Al_2CO_3(OH)_{16}\cdot 4$ ($H_2O$)) and activated carbon may be suitable for removal of such silicon containing compounds.

Temperatures in steps (ii), (iii) and (iv) may be in the range of from ambient temperature to 400° C., preferably of from 40 to 200° C., more preferably of from 40 to 180° C. Further, the pressure in steps (ii), (iii) and (iv) may be in the range from ambient to 100 bar, preferably in the range from 5 to 30 bar and most preferably in the range from 5 to 20 bar. Said pressure may be different than the pressure in washing step a), which step a) may include sorption step (i), and the pressure in extraction step b).

Heteroatom containing compounds and optionally aromatic hydrocarbons build up in sorbent material producing a "spent sorbent". As it is known in the art, eventually, it is required to replace or regenerate the sorbent. In either case, the corresponding vessel containing the spent sorbent is taken out of service. In case of regeneration, the spent sorbent is put in contact with a stream that does not contain heteroatom containing compounds and optionally aromatic hydrocarbons. Preferably, this stream is heated to facilitate the desorption of the heteroatom containing compounds and optionally aromatic hydrocarbons. The regeneration stream can be a gas, liquid or supercritical fluid. It can be inert such as nitrogen, or reactive such as hydrogen, oxygen and hydrogen peroxide. Depending on the regeneration method, regeneration temperatures are in the range of from 20 to 350° C. Regeneration of the sorbent material can be carried out by stripping with a stream such as steam, or nitrogen, or by heating the sorbent in air to burn off the sorbed material. Alternatively, in case the sorbent material used in the invention cannot be fully regenerated, it must be discarded when its sorption capacity is reached. Furthermore, for sorbents used in step a), when sorbent is separated as spent sorbent, the organic compounds contained in the sorbent can be removed by washing of the sorbent with an organic solvent as known in the art. Alternatively, the sorbent is removed for disposal like incineration.

Upstream and Downstream Integration

In the present invention, the liquid hydrocarbon feedstock stream may comprise at least part of a hydrocarbon product formed in a process comprising cracking of plastics, preferably waste plastics, more preferably mixed waste plastics, wherein at least part of the plastics comprises heteroatom containing organic compounds.

Accordingly, the present invention also relates to a process for the recovery of aliphatic hydrocarbons from plastics, wherein at least part of the plastics comprises heteroatom containing organic compounds, said process comprising the steps of:
(I) cracking the plastics and recovering a hydrocarbon product comprising aliphatic hydrocarbons, heteroatom containing organic compounds and optionally aromatic hydrocarbons; and
(II) subjecting a liquid hydrocarbon feedstock stream, which comprises at least part of the hydrocarbon product obtained in step (I), to the above-described process for the recovery of aliphatic hydrocarbons from a liquid hydrocarbon feedstock stream.

The preferences and embodiments as described above with reference to the present aliphatic hydrocarbons recovery process as such also apply to step (II) of the present process for the recovery of aliphatic hydrocarbons from plastics. In above-mentioned step (I), the resulting hydrocarbon product may be either a liquid or a solid or wax. In the latter case, the solid or wax is first heated to make it liquid, before subjecting it to the aliphatic hydrocarbons recovery process in step (II).

In the above-mentioned process, at least part of the plastics as fed to step (I) comprises heteroatom containing organic compounds, which plastics are preferably waste plastics, more preferably mixed waste plastics. In said step (I), the cracking of the plastics may involve a thermal cracking process and/or a catalytic cracking process. The cracking temperature in step (I) may be of from 300 to 800° C., suitably of from 400 to 800° C., more suitably of from 400 to 700° C., more suitably of from 500 to 600° C. Further, any pressure may be applied, which pressure may be sub-atmospheric, atmospheric or super-atmospheric. Heat treatment in step (I) causes melting of the plastics and cracking of its molecules into smaller molecules. The cracking in step (I) may be carried out as pyrolysis or as liquefaction. Both in pyrolysis and in liquefaction a continuous liquid phase is formed. In addition, in pyrolysis a discontinuous gas phase is formed that escapes the liquid phase and segregates into a continuous gas phase. In liquefaction, there is no significant gas phase by applying a relatively high pressure.

Further, in step (I), subsequent condensation of a gas phase and/or cooling of a liquid phase provides a hydrocarbon product, which may be either a liquid or a solid or wax, comprising aliphatic hydrocarbons, heteroatom containing organic compounds and optionally aromatic hydrocarbons, at least part of which is subjected to the above-described aliphatic hydrocarbons recovery process in step (II).

Above-described step (I) may be carried out in any known way, for example in a way as disclosed in WO2018069794 or in WO2017168165, the disclosures of which are herein incorporated by reference.

Advantageously, aliphatic hydrocarbons as recovered in one of the above-described processes for the recovery of aliphatic hydrocarbons, which may comprise varying amounts of aliphatic hydrocarbons within a wide boiling point range, may be fed to a steam cracker without a further pre-treatment, such as treatment with hydrogen (hydrotreating or hydroprocessing). In addition to being used as a feed to a steam cracker, said recovered aliphatic hydrocarbons may also advantageously be fed to other refining processes including hydrocracking, isomerization, hydrotreating, thermal catalytic cracking and fluid catalytic cracking. Further, in addition to being used as a feed to a steam cracker, said recovered aliphatic hydrocarbons may also advantageously be separated into different fractions which each may find a different application, such as diesel, marine fuel, solvent, etc.

Accordingly, the present invention also relates to a process for steam cracking a hydrocarbon feed, wherein the hydrocarbon feed comprises aliphatic hydrocarbons as recovered in one of the above-described processes for the recovery of aliphatic hydrocarbons. Further, accordingly, the present invention also relates to a process for steam cracking a hydrocarbon feed, comprising the steps of: recovering aliphatic hydrocarbons from a liquid hydrocarbon feedstock stream in one of the above-described processes for the recovery of aliphatic hydrocarbons; and steam cracking a hydrocarbon feed which comprises aliphatic hydrocarbons as recovered in the preceding step. In the present specification, said phrase "steam cracking a hydrocarbon feed which comprises aliphatic hydrocarbons as recovered in the preceding step" may mean "steam cracking a hydrocarbon feed which comprises at least part of the recovered aliphatic hydrocarbons". The hydrocarbon feed to the steam cracking process may also comprise hydrocarbons from another source, other than the present processes for the recovery of aliphatic hydrocarbons. Such other source may be naphtha, hydrowax or a combination thereof.

Advantageously, in a case wherein the liquid hydrocarbon feedstock stream comprises aromatic hydrocarbons, especially polycyclic aromatics, heteroatom containing organic compounds, conjugated aliphatic compounds having two or more carbon-carbon double bonds, or a combination thereof, these have already been removed by the present aliphatic hydrocarbons recovery process as described above before feeding recovered hydrocarbons to a steam cracking process. This is particularly advantageous in that said removed compounds, especially polycyclic aromatics, can no longer cause fouling in the preheat, convection and radiant sections of a steam cracker and in the downstream heat exchange and/or separation equipment for a steam cracker, for example in transfer line exchangers (TLEs) which are used to rapidly cool the effluent from a steam cracker. When hydrocarbons condense, they may thermally decompose into a coke layer which may cause fouling. Such fouling is a major factor determining the run length of the cracker. Reducing the amount of fouling results in longer run times without maintenance shutdowns, and improved heat transfer in the exchangers.

The steam cracking may be performed in any known way. The hydrocarbon feed is typically preheated. The feed can be heated using heat exchangers, a furnace or any other combination of heat transfer and/or heating devices. The feed is steam cracked in a cracking zone under cracking conditions to produce at least olefins (including ethylene) and hydrogen. The cracking zone may comprise any cracking system known in the art that is suitable for cracking the feed. The cracking zone may comprise one or more furnaces, each dedicated for a specific feed or fraction of the feed.

The cracking is performed at elevated temperatures, preferably in the range of from 650 to 1000° C., more preferably of from 700 to 900° C., most preferably of from 750 to 850° C. Steam is usually added to the cracking zone, acting as a diluent to reduce the hydrocarbon partial pressure and thereby enhance the olefin yield. Steam also reduces the formation and deposition of carbonaceous material or coke in the cracking zone. The cracking occurs in the absence of oxygen. The residence time at the cracking conditions is very short, typically in the order of milliseconds.

From the cracker, a cracker effluent is obtained that may comprise aromatics (as produced in the steam cracking process), olefins, hydrogen, water, carbon dioxide and other hydrocarbon compounds. The specific products obtained depend on the composition of the feed, the hydrocarbon-to-steam ratio, and the cracking temperature and furnace residence time. The cracked products from the steam cracker are then passed through one or more heat exchangers, often referred to as TLEs ("transfer line exchangers"), to rapidly reduce the temperature of the cracked products. The TLEs preferably cool the cracked products to a temperature in the range of from 400 to 550° C.

FIGURES

Figure 2:
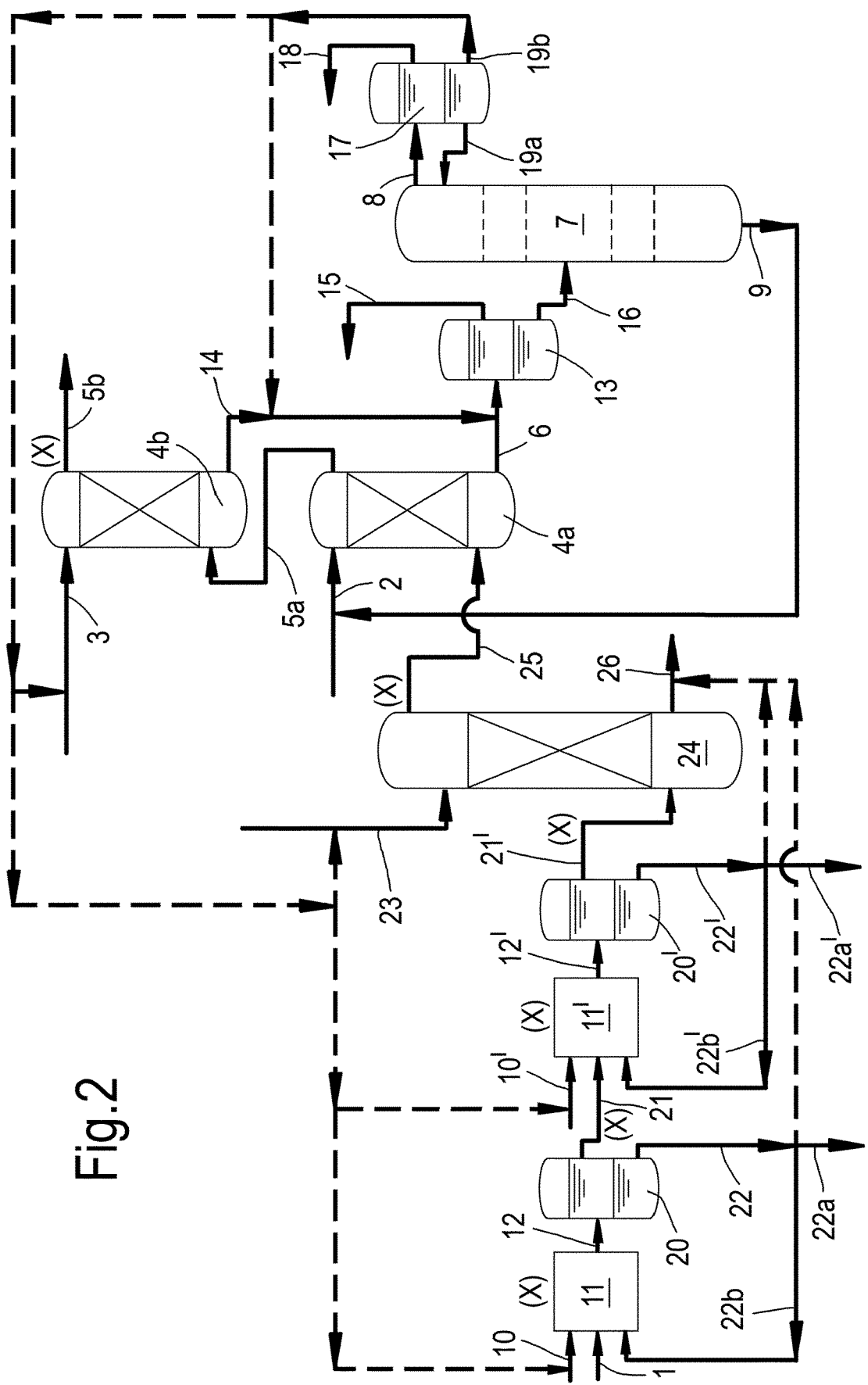
FIG. 2 shows another embodiment of the above-mentioned process.

The present process for the recovery of aliphatic hydrocarbons from a liquid hydrocarbon feedstock stream is further illustrated by FIGS. 1 and 2.

In the process of FIG. 1, a liquid hydrocarbon feedstock stream 1, which comprises aliphatic hydrocarbons (including conjugated aliphatic compounds having two or more carbon-carbon double bonds, which are hereinafter referred to as "dienes"), aromatic hydrocarbons, heteroatom containing organic compounds and salts, and a stream 10 which comprises water which is a washing solvent a) in accordance with the present invention and which has a pH below 7 (acid), are fed to and mixed in mixer 11. Further, as indicated in FIG. 1 by "(X)", a sorption agent may be fed to mixer 11, which represents optional sorption step (i) in accordance with the present invention.

The resulting mixed stream 12 is fed to a decanter 20. In decanter 20, the mixed stream is separated into a stream 21 comprising aliphatic hydrocarbons, dienes, aromatic hydrocarbons and heteroatom containing organic compounds and a stream 22 comprising water, heteroatom containing compounds and salts. Stream 22 is split into streams 22a and 22b, wherein stream 22b is recycled to mixer 11 optionally after removing organic compounds and salts from stream 22b. Stream 21 and a stream 10' which comprises water which is a washing solvent a) in accordance with the present invention and which has a pH above 7 (alkaline), are fed to and mixed in mixer 11'. As indicated in FIG. 1 by "(X)", stream 21 may be contacted with a sorption agent, which represents optional sorption step (ii) in accordance with the present invention. Further, as indicated in FIG. 1 by "(X)", a sorption agent may be fed to mixer 11', which represents optional sorption step (i) in accordance with the present invention.

The resulting mixed stream 12' is fed to a decanter 20'. In decanter 20', the mixed stream is separated into a stream 21' comprising aliphatic hydrocarbons, dienes, aromatic hydrocarbons and heteroatom containing organic compounds and a stream 22' comprising water, heteroatom containing compounds and salts. Stream 22' is split into streams 22a' and 22b', wherein stream 22b' is recycled to mixer 11' optionally after removing organic compounds and salts from stream 22b'. Stream 21' and a stream 23 which comprises water, which is a washing solvent a) in accordance with the present invention and which has a pH of about 7, are fed to an extraction column 24. Further, as indicated in FIG. 1 by "(X)", stream 21' may be contacted with a sorption agent, which represents optional sorption step (ii) in accordance with the present invention. In column 24, stream 21' is contacted with stream 23 (water), resulting in liquid-liquid extraction of heteroatom containing organic compounds with the water, resulting in a top stream 25 comprising aliphatic hydrocarbons, dienes, aromatic hydrocarbons and heteroatom containing organic compounds and a bottom stream 26 comprising water and heteroatom containing compounds. Stream 26 may be combined with part of stream 22 from decanter 20. Further, as indicated in FIG. 1 by "(X)", stream 25 may be contacted with a sorption agent, which represents optional sorption step (iii) in accordance with the present invention.

Further, in the process of FIG. 1, stream 25 from extraction column 24; a first solvent stream 2 which comprises an organic solvent (for example N-methylpyrrolidone) which is an extraction solvent b) in accordance with the present invention; and a second solvent stream 3 which comprises water which is a washing solvent, are fed to an extraction column 4. In column 4, stream 25 is contacted with first solvent stream 2 (organic solvent), thereby recovering aliphatic hydrocarbons by liquid-liquid extraction of dienes, aromatic hydrocarbons and heteroatom containing organic compounds with the organic solvent. Further, the water in second solvent stream 3 removes organic solvent from the upper part of column 4 by liquid-liquid extraction of organic solvent with water. A stream 5 comprising recovered aliphatic hydrocarbons exits column 4 at the top. Further, a stream 6 comprising organic solvent, water, dienes, aromatic hydrocarbons and heteroatom containing organic compounds exits column 4 at the bottom. As indicated in FIG. 1 by "(X)", stream 5 may be contacted with a sorption agent, which represents optional sorption step (iv) in accordance with the present invention. Stream 6 and a stream 14 comprising additional water, which is a demixing solvent, are combined, and the combined stream is fed to a decanter 13. In decanter 13, the combined stream is separated into a stream 15 comprising dienes, aromatic hydrocarbons and heteroatom containing organic compounds and a stream 16 comprising organic solvent, water, dienes, aromatic hydrocarbons and heteroatom containing organic compounds. Stream 16 is fed to a distillation column 7, where it is separated into a top stream 8 comprising water, dienes, aromatic hydrocarbons and heteroatom containing organic compounds and a bottom stream 9 comprising organic solvent. Organic solvent from bottom stream 9 is recycled via organic solvent stream 2. Stream 8 is fed to an overhead decanter 17, wherein it is separated into a stream 18 comprising dienes, aromatic hydrocarbons and heteroatom containing organic compounds and a stream comprising water, which may additionally comprise a relatively low amount of dienes, aromatic hydrocarbons and heteroatom containing organic compounds, part of which water stream (stream 19a) is sent back to distillation column 7 as a reflux stream whereas the other part (stream 19b) may be recycled via water stream 14 and/or water stream 3 and/or water stream 10 and/or water stream 23.

In the process of FIG. 2, the above-mentioned liquid hydrocarbon feedstock stream 1 is also first contacted with water, which is a washing solvent a) in accordance with the present invention, first in a mixer 11 and a decanter 20, then in a mixer 11' and a decanter 20', and subsequently in an extraction column 24. In respect of such upstream treatments of said feedstock stream in the process of FIG. 2 reference is made to the above description of the corresponding treatments in the process of FIG. 1, also including optional contacting with a sorption agent as indicated in FIG. 2 by "(X)" in connection with mixers 11 and 11', streams 21 and 21' and stream 25, representing sorption steps (i), (ii) and (iii) in accordance with the present invention.

Further, in the process of FIG. 2, stream 25 from extraction column 24 which comprises aliphatic hydrocarbons, dienes, aromatic hydrocarbons and heteroatom containing organic compounds; and a first solvent stream 2 which comprises an organic solvent (for example N-methylpyrrolidone) which is an extraction solvent b) in accordance with the present invention, are fed to a first extraction column 4a. In column 4a, stream 25 is contacted with first solvent stream 2 (organic solvent), thereby recovering aliphatic hydrocarbons by liquid-liquid extraction of dienes, aromatic hydrocarbons and heteroatom containing organic compounds with the organic solvent, resulting in a top stream 5a comprising recovered aliphatic hydrocarbons and organic solvent and a bottom stream 6 comprising organic solvent, dienes, aromatic hydrocarbons and heteroatom containing organic compounds. Stream 5a and a second solvent stream 3 which comprises water, which is a washing solvent, are fed to a second extraction column 4b. In column 4b, stream 5a is contacted with second solvent stream 3 (water), thereby removing organic solvent by liquid-liquid extraction of organic solvent with water. A stream 5b comprising recovered aliphatic hydrocarbons exits column 4b at the top. Further, a stream 14 comprising organic solvent and water, which water is a demixing solvent, exits column 4b at the bottom. As indicated in FIG. 2 by "(X)", stream 5b may be contacted with a sorption agent, which represents optional sorption step (iv) in accordance with the present invention. Streams 6 and 14 are combined, and the combined stream is fed to a decanter 13. In respect of the treatment in decanter 13 and further, downstream treatments in the process of FIG. 2 reference is made to the above description of the corresponding treatments in the process of FIG. 1.

We claim:

1. A process for the recovery of aliphatic hydrocarbons from a liquid hydrocarbon feedstock stream comprising aliphatic hydrocarbons, heteroatom containing organic compounds and optionally aromatic hydrocarbons, said process comprising the steps of:
   a) mixing at least part of the liquid hydrocarbon feedstock stream with a stream having a pH above 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons,
   said step a) further comprising:
   a1) before mixing with the stream having a pH above 7: mixing at least part of the liquid hydrocarbon feedstock stream with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and mixing at least part of said second stream with the stream having a pH above 7, and/or
   a2) after mixing with the stream having a pH above 7: mixing at least part of the second stream, resulting from the mixing with the stream having a pH above 7 and the separation into first and second streams, with a stream having a pH below 7 and comprising a washing solvent a) which contains one or more heteroatoms and separating the resulting mixture into a first stream comprising washing solvent a) and heteroatom containing compounds and a second stream comprising aliphatic hydrocarbons, heteroatom containing organic compounds and optionally aromatic hydrocarbons, and feeding at least part of said second stream to step b); and
   b) contacting at least part of the second stream resulting from step a) with an extraction solvent b) which contains one or more heteroatoms and subjecting that stream to liquid-liquid extraction with extraction solvent b), resulting in a first stream comprising aliphatic hydrocarbons and optionally heteroatom containing organic compounds and a second stream comprising extraction solvent b), heteroatom containing organic compounds and optionally aromatic hydrocarbons.

2. The process according to claim 1, wherein:
   the washing solvent a) has a Ra,heptane of at least 10 $MPa^{1/2}$, wherein Ra,heptane refers to the Hansen solubility parameter distance with respect to heptane as determined at 25° C.; and
   the washing solvent a) has a solubility of sodium chloride, in g of NaCl per 100 g of solvent as determined at 25° C., of at least 0.1 g/100 g.

3. The process according to claim 1, wherein the washing solvent a) comprises one or more solvents selected from the group consisting of water, ammonia and organic solvents selected from the group consisting of diols and triols, including monoethylene glycol (MEG), monopropylene glycol (MPG) and glycerol; glycol ethers, including oligoethylene glycols, including diethylene glycol, triethylene glycol and tetraethylene glycol, and polyethylene glycols (PEG) which may have a molecular weight of 200 to 1,000 g/mole or 200 to 700 g/mole; amides, including formamide and monoalkyl formamides and acetamides, wherein the alkyl group contain 1 to 8 or 1 to 3 carbon atoms, including methyl formamide; dialkylsulfoxide, wherein the alkyl group may contain 1 to 8 or 1 to 3 carbon atoms, including dimethylsulfoxide (DMSO); sulfones, including sulfolane; hydroxy esters, including lactates, including methyl and ethyl lactate; aminic compounds, including ethylenediamine, monoethanolamine, diethanolamine and triethanolamine; carbonate compounds, including propylene carbonate and glycerol carbonate; and cycloalkanone compounds, including dihydrolevoglucosenone.

4. The process according to claim 1, wherein:
   the extraction solvent b) has a Ra,heptane of at least 5 $MPa^{1/2}$, wherein Ra,heptane refers to the Hansen solubility parameter distance with respect to heptane as determined at 25° C.

5. The process according to claim 1, wherein the extraction solvent b) comprises ammonia or one or more organic solvents selected from the group consisting of diols and triols, including monoethylene glycol (MEG), monopropylene glycol (MPG), any isomer of butanediol and glycerol; glycol ethers, including oligoethylene glycols, including diethylene glycol, triethylene glycol and tetraethylene glycol, and monoalkyl ethers thereof, including diethylene glycol ethyl ether; amides, including N-alkylpyrrolidone, wherein the alkyl group may contain 1 to 8 or 1 to 3 carbon atoms, including N-methylpyrrolidone (NMP), formamide and di-and monoalkyl formamides and acetamides, wherein the alkyl group may contain 1 to 8 or 1 to 3 carbon atoms, including dimethyl formamide (DMF), methyl formamide and dimethyl acetamide; dialkylsulfoxide, wherein the alkyl group contain 1 to 8 or 1 to 3 carbon atoms, including dimethylsulfoxide (DMSO); sulfones, including sulfolane; N-formyl morpholine (NFM); furan ring containing components and derivatives thereof, including furfural, 2-methyl-furan, furfuryl alcohol and tetrahydrofurfuryl alcohol; hydroxy esters, including lactates, including methyl and ethyl lactate; trialkyl phosphates, including triethyl phosphate; phenolic compounds, including phenol and guaiacol; benzyl alcoholic compounds, including benzyl alcohol; aminie compounds, including ethylenediamine, monoethanolamine, diethanolamine and triethanolamine; nitrile compounds, including acetonitrile and propionitrile; trioxane compounds, including 1,3,5-trioxane; carbonate compounds, including propylene carbonate and glycerol carbonate; and cycloalkanone compounds, including dihydrolevoglucosenone.

6. The process according to claim 1, wherein:
(i) during step a), at least part of the liquid hydrocarbon feedstock stream is contacted with a sorption agent before the first and second streams are separated in step a);
and/or
(ii) between a preceding step a) and a subsequent step a), at least part of the second stream resulting from the preceding step a) is contacted with a sorption agent; and/or
(iii) between steps a) and b), at least part of the second stream resulting from step a) is contacted with a sorption agent; and/or
(iv) the first stream resulting from step b) comprises aliphatic hydrocarbons and heteroatom containing organic compounds and, after step b), at least part of that stream is contacted with a sorption agent.

7. The process according to claim 6, wherein:
(i) part of the heteroatom containing organic compounds is removed from the liquid hydrocarbon feedstock stream by contacting at least part of that stream with a sorption agent during step a) before the first and second streams are separated in step a), and at least part of the treated stream resulting from step (i) is fed to step b); and/or
(ii) part of the heteroatom containing organic compounds is removed from the second stream resulting from a preceding step a) by contacting at least part of that stream with a sorption agent, and at least part of the treated stream resulting from step (ii) is fed to a subsequent step a); and/or
(iii) part of the heteroatom containing organic compounds is removed from the second stream resulting from step a) by contacting at least part of that stream with a sorption agent, and at least part of the treated stream resulting from step (iii) is fed to step b); and/or
(iv) the first stream resulting from step b) comprises aliphatic hydrocarbons and heteroatom containing organic compounds, and heteroatom containing organic compounds are removed from that stream by contacting at least part of that stream with a sorption agent.

8. A process for the recovery of aliphatic hydrocarbons from plastics, wherein at least part of the plastics comprises heteroatom containing organic compounds, said process comprising the steps of:
(I) cracking the plastics and recovering a hydrocarbon product comprising aliphatic hydrocarbons, heteroatom containing organic compounds and optionally aromatic hydrocarbons; and
(II) subjecting a liquid hydrocarbon feedstock stream, which comprises at least part of the hydrocarbon product obtained in step (I), to the process of claim 1.

9. Process for steam cracking a hydrocarbon feed, wherein the hydrocarbon feed comprises aliphatic hydrocarbons as recovered in a process according to claim 1.

10. Process for steam cracking a hydrocarbon feed, comprising the steps of:
recovering aliphatic hydrocarbons from a liquid hydrocarbon feedstock stream in a process according to claim 1; and
steam cracking a hydrocarbon feed which comprises aliphatic hydrocarbons as recovered in the preceding step.

* * * * *